United States Patent
Kim et al.

(10) Patent No.: US 9,089,554 B2
(45) Date of Patent: Jul. 28, 2015

(54) COMPOSITION COMPRISING EXPRESSION OR ACTIVITY REGULATORS OF AKAP12 FOR TREATING CENTRAL NERVE SYSTEM DISEASES

(75) Inventors: Kyu-Won Kim, Seoul (KR); Jong-Ho Cha, Seoul (KR)

(73) Assignee: SNU R&B Foundation, Seoul (KR)

( * ) Notice: Subject to any disclaimer, the term of this patent is extended or adjusted under 35 U.S.C. 154(b) by 0 days.

(21) Appl. No.: 14/000,587

(22) PCT Filed: Feb. 21, 2012

(86) PCT No.: PCT/KR2012/001319
§ 371 (c)(1),
(2), (4) Date: Aug. 20, 2013

(87) PCT Pub. No.: WO2012/115439
PCT Pub. Date: Aug. 30, 2012

(65) Prior Publication Data
US 2013/0330361 A1    Dec. 12, 2013

(30) Foreign Application Priority Data

Feb. 25, 2011  (KR) .................. 10-2011-0017086
Nov. 18, 2011  (KR) .................. 10-2011-0120889

(51) Int. Cl.
| | | |
|---|---|---|
| *A01N 37/18* | (2006.01) | |
| *A61K 38/00* | (2006.01) | |
| *A61K 39/395* | (2006.01) | |
| *C12N 15/113* | (2010.01) | |

(52) U.S. Cl.
CPC .......... *A61K 39/3955* (2013.01); *C12N 15/113* (2013.01); *C12N 2310/14* (2013.01)

(58) Field of Classification Search
None
See application file for complete search history.

(56) References Cited

U.S. PATENT DOCUMENTS

| | | |
|---|---|---|
| 2006/0154330 A1 | 7/2006 | Klussmann et al. |
| 2008/0248008 A1 | 10/2008 | Carlson et al. |
| 2009/0176773 A1 | 7/2009 | Klussmann et al. |

FOREIGN PATENT DOCUMENTS

| | | |
|---|---|---|
| KR | 10-2004-0108321 | 12/2004 |
| WO | 2009/151304 | 12/2009 |

OTHER PUBLICATIONS

Hiromi Takaki et al., J. Biol. Chem., 2008, 283(22):14955-62.*
Cao et al., Blood, 2003, 101(2):498-507.*
Buisson et al., Cell. Mol. Neurobiol., 2003, 23(4/5):539-50.*
Shen et al., J. Neurosci. Res., 2009, 87:545-55.*
Notice of Allowance dated Feb. 19, 2014 received in Korean Patent Application No. 2011-0120889.

* cited by examiner

*Primary Examiner* — Olga N Chernyshev
(74) *Attorney, Agent, or Firm* — Riverside Law LLP

(57) ABSTRACT

The invention includes a pharmaceutical composition comprising an expression or activity regulator of AKAP12 (A-kinase anchoring protein 12) as the active ingredient. The compositions of the invention are useful for treating central nervous system diseases. The invention further includes a method of treating central nervous system diseases using a pharmaceutical composition of the invention. The central nervous system diseases contemplated within the invention include post-traumatic stress syndrome, stroke, and spinal injury.

3 Claims, 24 Drawing Sheets

Fig. 9
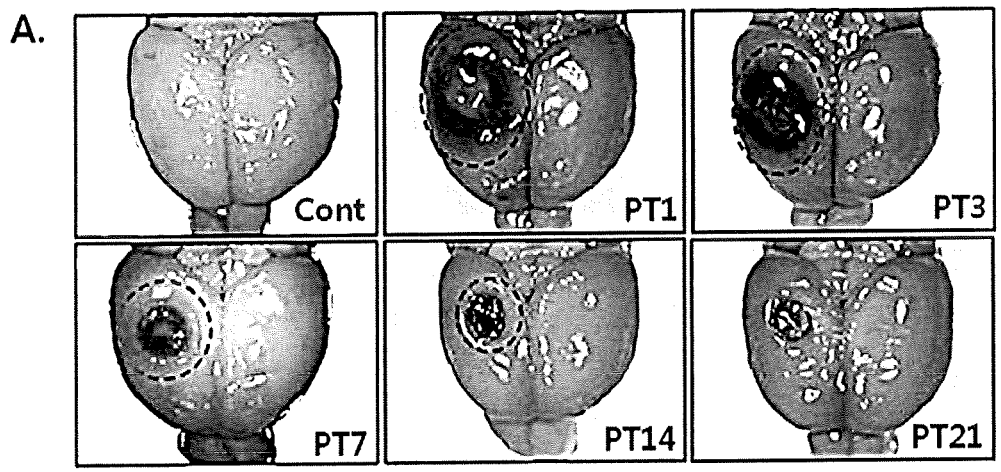
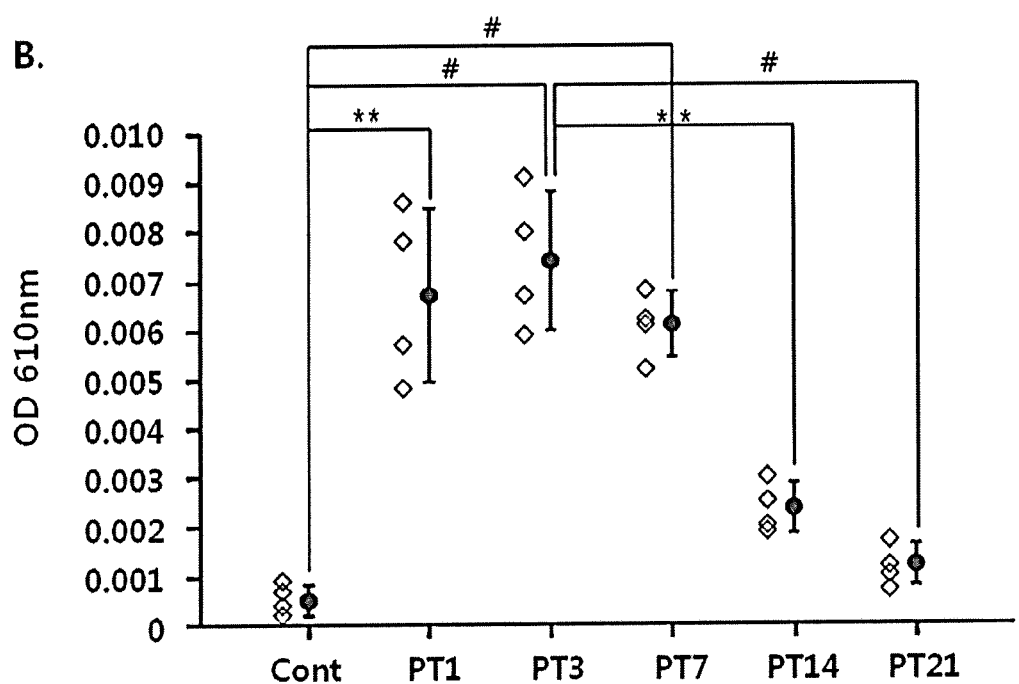
P*<0.01, P**<0.05, P#<0.001

Fig. 12
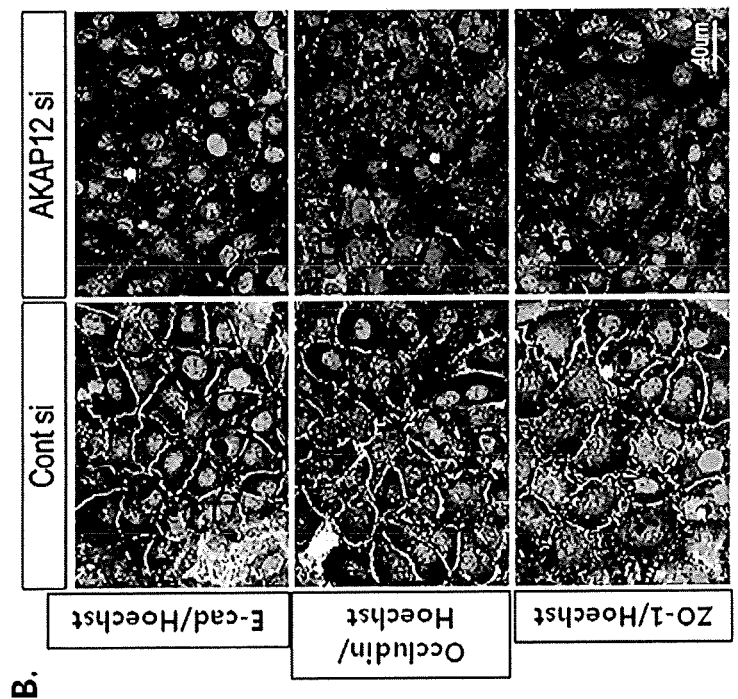
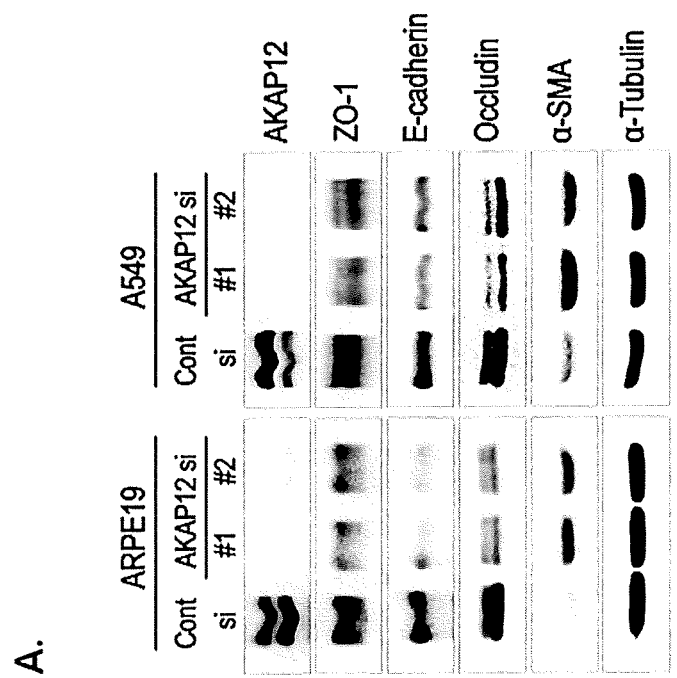

COMPOSITION COMPRISING EXPRESSION OR ACTIVITY REGULATORS OF AKAP12 FOR TREATING CENTRAL NERVE SYSTEM DISEASES

CROSS-REFERENCE TO RELATED APPLICATIONS

The present application is a 35 U.S.C. §371 national phase application of, and claims priority to, International Application No. PCT/KR12/001319, filed Feb. 21, 2012, and published under PCT Article 21(2) in English, which claims priority to Korean Applications No. 10-2011-0017086, filed Feb. 25, 2011, and No. 10-2011-0120889, filed Nov. 18, 2011, all of which applications are hereby incorporated by reference in their entireties herein.

TECHNICAL FIELD

The present invention relates to a pharmaceutical composition for the treatment of central nervous system diseases comprising an expression or activity regulator of AKAP12 (A-kinase anchoring protein 12) as an active ingredient, and a method for the treatment of central nervous system diseases using the same.

BACKGROUND ART

The treatment of central nervous system diseases, such as post-traumatic stress syndrome, resulting mostly from traffic accidents, stroke, spinal cord injury, etc., has typically resorted to surgical operations and physical modalities while waiting expectedly for the advent of effective therapeutic drugs. The mechanism of recovery from injury commonly found in the diseases induced by central nervous system injury is the formation of fibrotic-glial scars. The fibrotic-glial scars serve as a kind of physiological barrier which act to confine inflammatory activity to the injured tissues so as to minimize the secondary injury induced by inflammation. In the art, accordingly, controlling the formation of fibrotic-glial scars is recognized as playing an important role in the treatment and/or improving the prognosis of central nervous system injury-induced diseases.

AKAP12 (A-Kinase anchoring protein 12), a member of the scaffolding protein family and present within cells, is known to be down-regulated in response to the activation of oncogenes such as src or ras. Particularly in association with a β-adrenergic receptor, PKC, PKA, and F-actin, AKAP12 is involved in signaling pathways. Also, it is reported that AKAP12 participates in cell migration, mitosis, and the regulation of blood barrier formation and apoptosis. However, nowhere have the roles and/or functions of AKAP12 in the formation of fibrotic-glial scars been mentioned in previous documents, thus far.

DISCLOSURE OF INVENTION

Technical Problem

Culminating in the present invention, intensive and thorough research into AKAP12 that was conducted by the present inventors resulted in the finding that AKAP12 plays a pivotal role in the formation of fibrotic-glial scars and that the down-regulation of AKAP12 expression gives rise to excessive inflammation which induces the occurrence of secondary injury.

It is therefore an object of the present invention to provide a composition and a method for treating injury-induced central nervous system diseases.

Solution to Problem

In accordance with an aspect thereof, the present invention provides a pharmaceutical composition for the treatment of central nervous system diseases, comprising an expression regulator or an activity regulator of AKAP as an active ingredient.

"Central nervous system diseases" may include stroke, traumatic cerebral diseases and spinal injury diseases.

In an embodiment, the composition may further comprise a pharmaceutically acceptable carrier.

In accordance with another aspect thereof, the present invention provides a method for the treatment of central nervous system diseases, comprising administering an expression or activity regulator of AKAP12 in a pharmaceutically effective amount to a subject in need thereof.

In an embodiment, the method may further comprise administering an anti-inflammatory agent to the subject.

In accordance with a further aspect thereof, the present invention provides the use of an expression or activity regulator of AKAP 12 (A-kinase anchoring protein 12) for the treatment of central nervous system diseases.

Advantageous Effects of Invention

Having the ability to up- or down-regulate the formation of fibrotic-glial scars which are absolutely central to the regulation of central nervous system diseases, as described above, the pharmaceutical composition of the present invention comprising an expression or activity regulator of AKAP12 can be used to effectively treat central nervous system diseases by reducing excessive inflammation-induced secondary injury and by promoting the regeneration of the neural network. Ultimately, the expression or activity regulator of AKAP12 in accordance with the present invention is expected to be used in the treatment and prognosis improvement of central nervous system diseases including post-traumatic stress syndrome, stroke, and spinal injury.

BRIEF DESCRIPTION OF DRAWINGS

FIG. 9, comprising FIGS. 9A-9B, shows a functional establishment process of the fibrotic-glial scar as a physiological barrier with time after cerebral injury: Evans blue dye was injected 1, 3, 7, 14 and 21 days after cerebral injury and allowed to penetrate the cerebral tissue.

FIGS. 10A-10B, shows comparison of the function of the fibrotic-glial scar as a physiological barrier between AKAP12-knockout mice (KO) and wild-type mice (WT), demonstrating that AKAP12 plays an important role in the establishment of glial scars which act as a physiological barrier.

FIG. 12, comprising FIGS. 11A-11B, shows a decrease in the expression level of the stabilization related proteins (ZO-1, Occludin, Ecadherin) and an increase in the expression level of the activation related protein ($\alpha$-SMA) upon the down-regulation of AKAP12, at the cellular level, which is the same at the tissue level.

FIGS. 13A-13C, shows an increase in the expression level of SNAI1, a representative cell activator, upon the down-regulation of AKAP12.

BEST MODE FOR CARRYING OUT THE INVENTION

Figure 1:
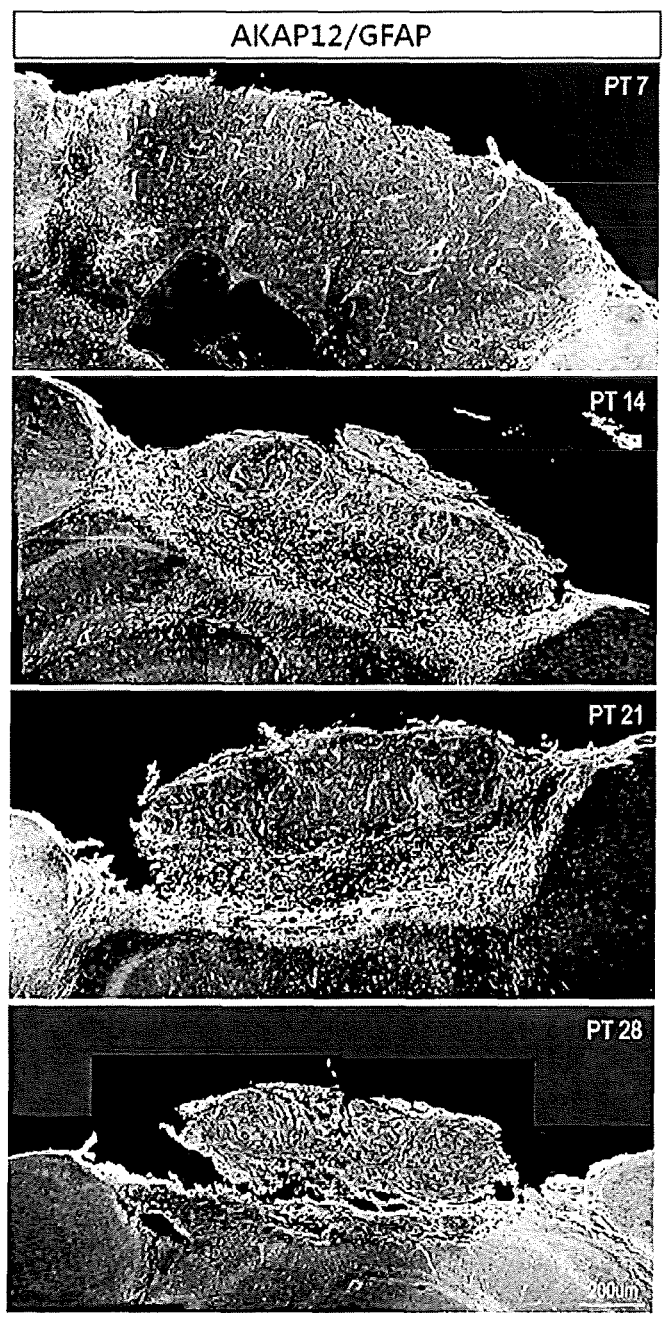
FIG. 1 shows a formation process of fibrotic-glial scars and an expression pattern of AKAP12 with respect to the time (one week (PT7), two weeks (PT14), three weeks (PT27) and four weeks (PT28)) after cerebral injury.

The present invention pertains to a pharmaceutical composition for the treatment of central nervous system diseases, comprising an expression or activity regulator of AKAP12. The present invention is based on the discoveries that, first, AKAP12 is involved in the formation and/or suppression of fibrotic-glial scarring which is the normal mechanism of recovery from injury found in the diseases induced by central nervous system injury and, secondly, that when the expression of AKAP12 is down-regulated, excessive inflammation occurs, giving rise to secondary injury.

Functioning to confine inflammation to only injured tissues, fibrotic-glial scars serve as a kind of physiological barrier that minimizes the inflammation-induced secondary injury. AKAP12 is an intracellular scaffolding protein the expression of which is down-regulated in response to an oncogene such as src or ras.

Under the condition of the central nervous system having been injured, an examination was made of the formation of fibrotic-glial scars and of the role of AKAP12 in their formation.

To this end, first, a cerebral tissue was locally damaged using a photothrombosis mouse model. The formation of fibrotic-glial scars and the expression levels of AKAP12 were monitored over time. As a result, it was discovered that both cerebral meninges-derived fibroblasts, predominantly found in fibrotic-glial scars, and cerebral astrocytes migrate into the inflammatory tissue to form two separate layers which isolate the inflammatory tissue from adjacent cerebral tissues and that there was a high level of expression of AKAP12 in the scar thus formed (see FIG. 1).

After being elaborately excised, the fibrotic-glial scar region was subjected to Western blotting. In the early stage where inflammation intensively deepens and main constitutional cells of the fibrotic-glial scars migrate in response to inflammation signals, the expression level of AKAP12 was observed to be decreased. However, the expression of AKAP12 increased in the late stage wherein the scaffold of the fibrotic-glial scar became sturdy (see FIG. 2).

In this context, the expression of AKAP12 in relation to the time at which fibrotic-glial scars formed was closely investigated. In the early stage of injury where a number of cerebral meninges-derived fibroblasts infiltrated into the inflammatory tissue, the expression of AKAP12 was detected in a small number of the cells. In contrast, almost all fibroblasts were found to express AKAP12 in the late stage where the scaffold of the scar was completed. Likewise, astrocytes, which have a low expression level of AKAP12 in a normal state, were observed to have an increased expression level of AKAP12 when they were activated into reactive astrocytes by an inflammation signal. A peak in the AKAP12 expression level was detected in the reactive astrocytes which migrated into inflammatory regions and had become entangled with each other to form a scar (see FIGS. 3 and 4).

A research report has it that when the expression of AKAP12 decreases, cancer increases in motility and thus is apt to metastasize. Hence, it could be understood from the research data that cerebral meninges-derived cells in a stable state would be decreased in the expression level of AKAP12 by an inflammation signal and become actively motile so that they are apt to infiltrate into the cerebral tissue, and when the expression level of AKAP12 in cells recovers, they are stabilized, with the scaffold of the scar being completed.

Fibrotic-glial scarring is a scaffold which is formed upon the central nervous system being injured. Serving as a barrier that isolates inflammatory regions from normal tissues, the fibrotic-glial scars prevent the normal tissues from being secondarily injured by inflammation. The fact that both cerebral meninges-derived fibroblasts and cerebral astrocytes, which are predominantly present in the scaffold, have an increased expression level of AKAP12 indicates that there is a relationship between the function of fibrotic-glial scars and AKAP12.

To ascertain the relationship between AKAP12 with the function of fibrotic-glial scar, the expression levels of all of occludin, E-cadherin, and ZO-1, which all play an important role in the function of the fibrotic-glial scar as a physiological barrier, were monitored.

Normal cell layers are formed as a result of the simple aggregation of cells and play a limited role as a physiological barrier. In a cell layer that accounts for a practical physiological barrier, cells show a high expression level of specific proteins. These proteins are linked from one cell to another in the cell layer, forming cell-cell junctions through which intercellular adhesion is reinforced. At the junction, occludin and E-cadherin which are embedded in the cell membrane of one cell bind directly to those on another cell. Assuming that cells are bricks, occluding and E-cadherin serve as mortar which tightly binds bricks together. ZO-1, a tight junction protein present beneath the cell membrane, acts to interact with various proteins located at the junction. Accordingly, when occludin, E-cadherin, and ZO-1 are expressed at low levels, the cell-cell junction becomes loose so that the function of the cell layer as a physiological barrier is lost.

Figure 6:
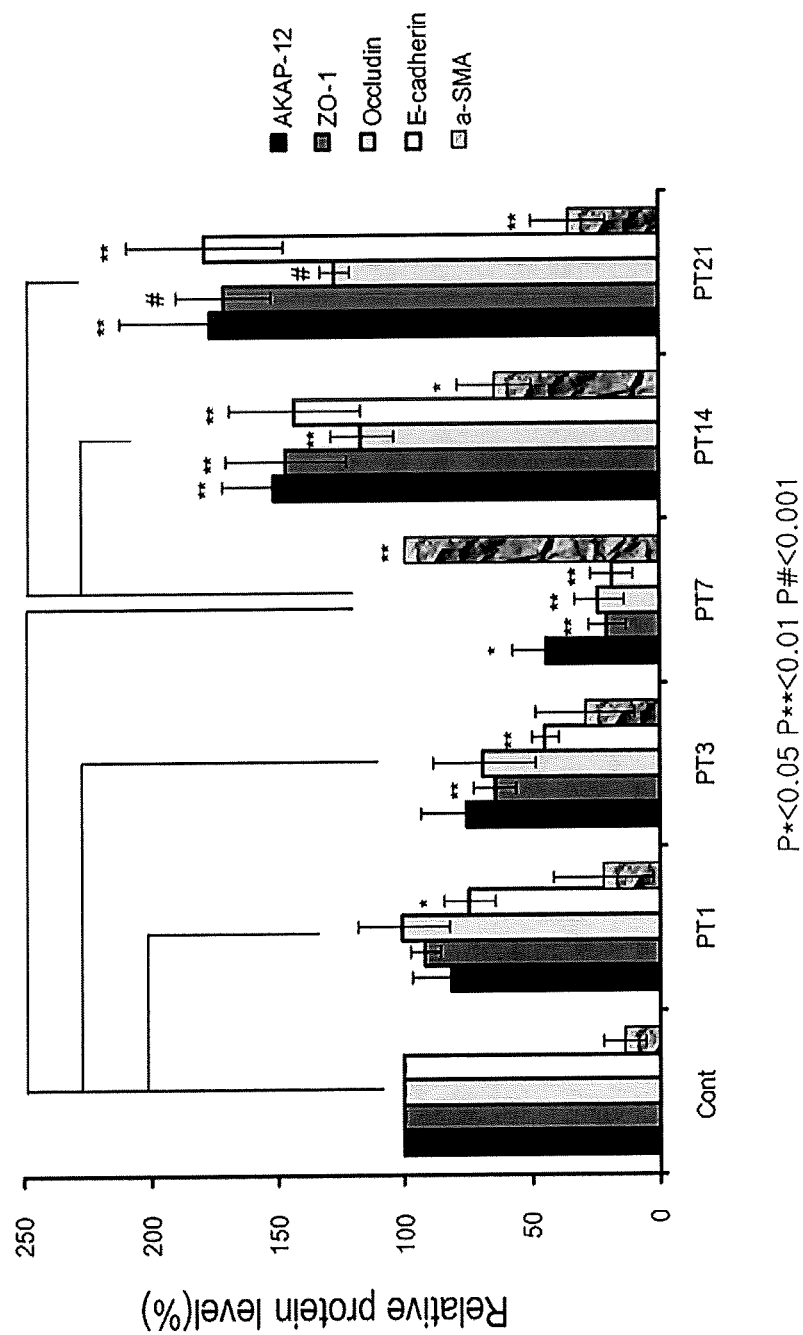
FIG. 6 is a graph showing the expression levels of various marker proteins in fibrotic-glial scar that was elaborately dissected from the brain excised 1, 3, 7, 14, and 21 days after cerebral injury.
Figure 7:
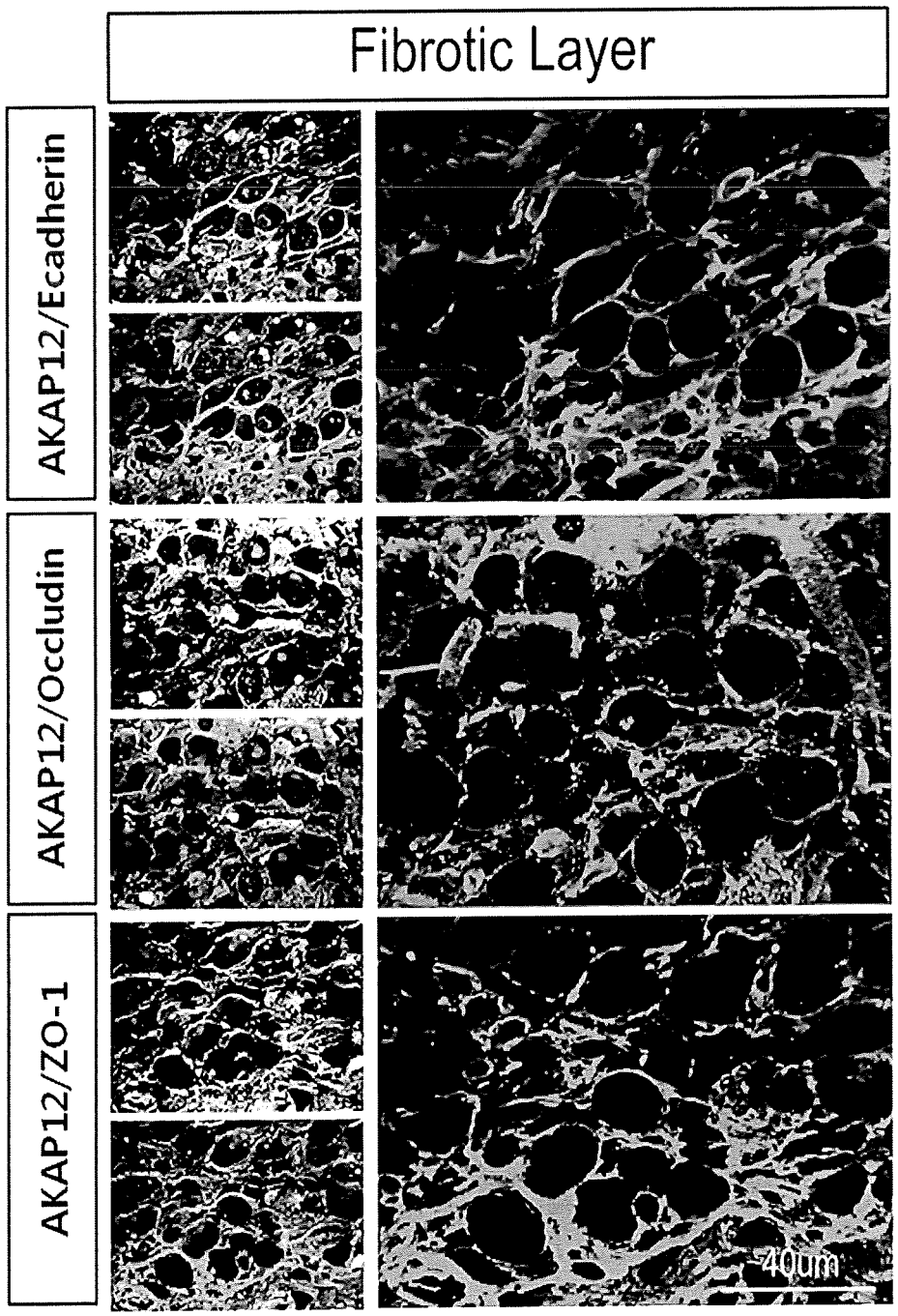
FIG. 7 is of fluorescence photographs showing that ZO-1, occludin and E-cadherin, which are all responsible for cell to cell junction and play an important role in the establishment of a cell layer functioning as a physiological barrier, were expressed in the cerebral meninges-derived fibroblasts which overexpressed AKAP12.
Figure 8:
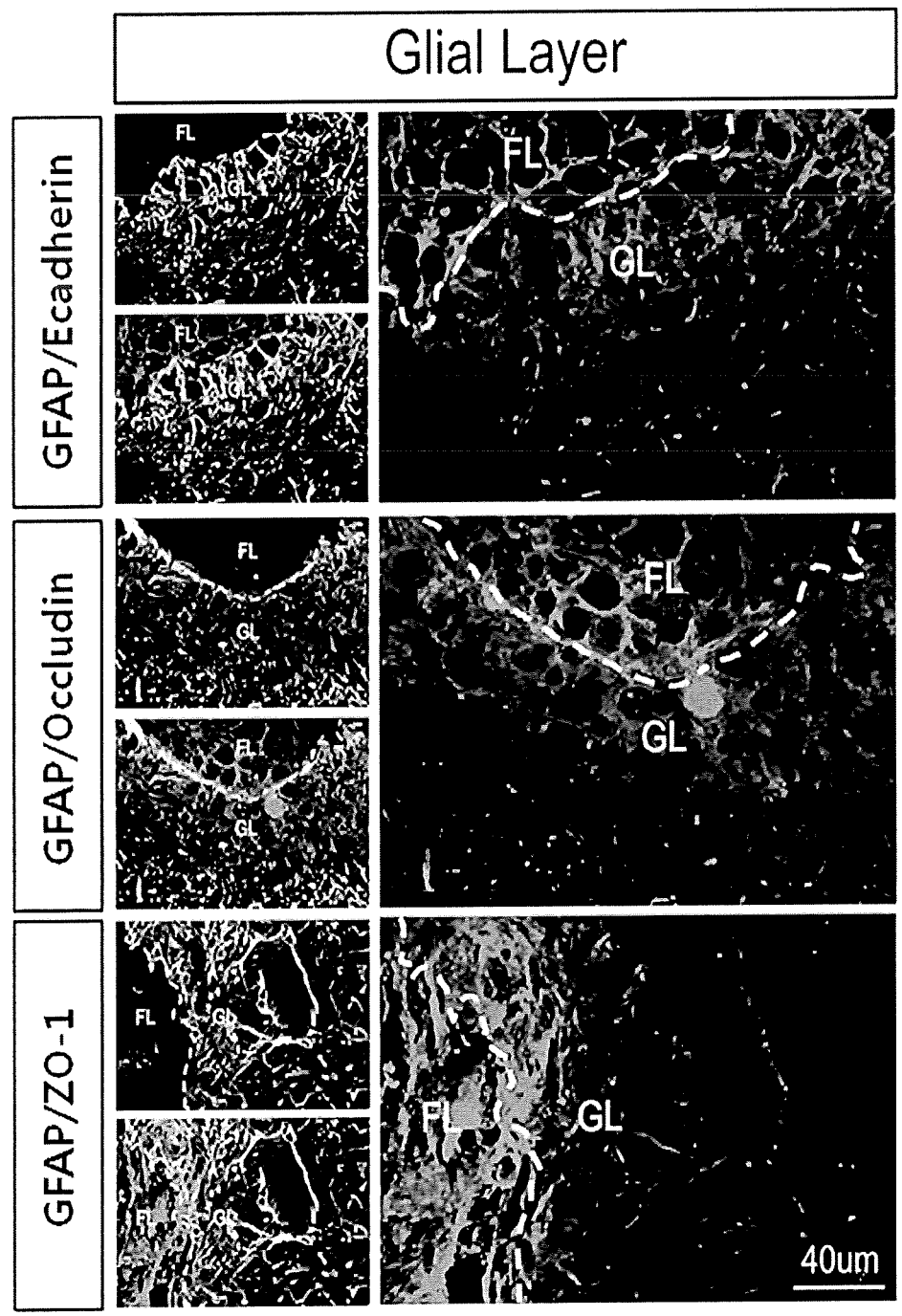
FIG. 8 is of fluorescence photographs showing that ZO-1, occludin and E-cadherin, which are all responsible for cell-to-cell junctions and play an important role in the establishment of a cell layer functioning as a physiological barrier, were expressed in the reactive astrocytes which overexpressed AKAP12.

In the present invention, occludin, E-cadherin, and ZO-1 were found to be expressed in the same pattern as AKAP12 (see FIG. 6). It was also found that all occludin, E-cadherin and ZO-1 are expressed in the cerebral meninges-derived fibroblasts and the reactive astrocytes which both overexpress AKAP12 (see FIGS. 7 and 8).

To identify the role of AKP12 in the formation of fibrotic-glial scars, the formation of fibrotic-glial scars in wild-type mice and AKAP12-knockout mice was compared. In the AKAP12-KO mice, inflammatory factors or cells leaked into tissues surrounding the fibrotic-glial scar to cause the blood brain barrier to collapse, indicating that AKAP12-KO mice have a problem in the formation of fibrotic-glial scars (see FIG. 10).

Figure 11:
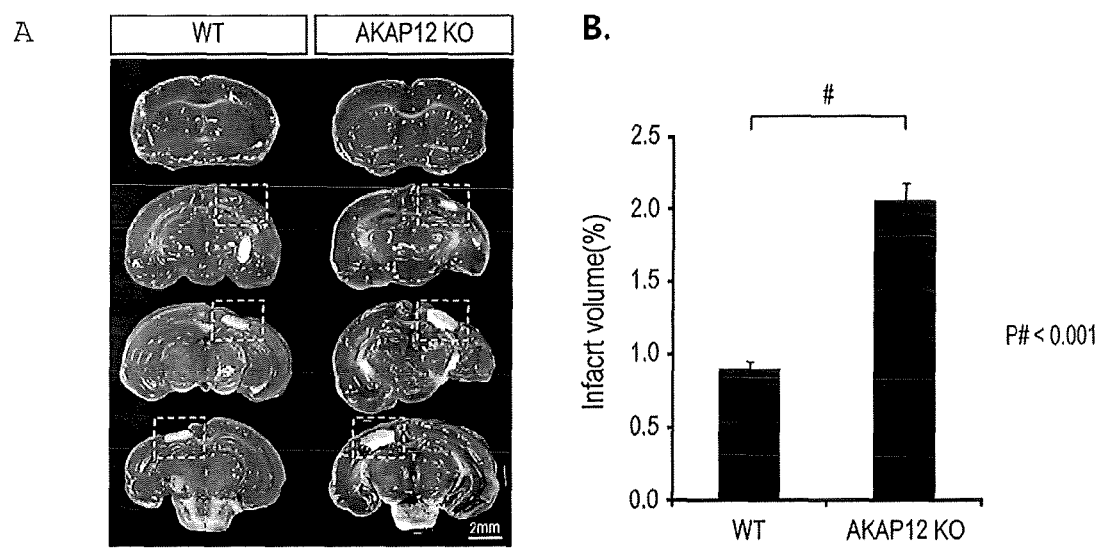
FIG. 11, comprising FIGS. 11A-11B, compares the degree of tissue injury between AKAP12-knockout mice (KO) and wild-type mice (WT).

A TCC staining test showed that the tissue infarct size of the KO mice was about twice as large as that of wild-type mice (see FIG. 11).

In addition, an experiment was conducted to examine the mechanism of AKAP12 activity. Epithelial cells form the epithelium which primarily serves as a physiological barrier to separate the organ from external environments. Epithelial cells are attached to each other at many locations by many tight junctions and are in a stabilized state, with little motility. Mesenchymal cells, which typically refer to fibroblasts, lack junctions and thus are of high motility. EMT (Epithelial Mesenchymal Transition) is one of the most important events which occur when a new organ is formed in the development stage or when a physiological barrier is regenerated after a tissue has been injured by a disease. When receiving development or inflammation signals, the epithelium, forms a stable structure but also loses its epithelial properties and obtains mesenchymal properties. The resulting transformed cells proliferate actively and migrate to a suitable site. After a proper number of the cells have gathered together at a suitable site, if the development or inflammation signal is reduced or disappears, the mesenchymal cells return back to epithelial cells to form a new physiological barrier. Consequently, the phenomenon that the present inventors observed after brain injury is the regeneration of the cerebral meninges as a physiological barrier in which AKAP12 is involved. Accordingly, the role of AKAP12 in EMT needed to be ascertained at a cellular level. Because there are various types of cells in the cerebral meninges, it is difficult to separate out from the cerebral meninges only cells of epithelial properties. Further, no epithelial cell lines are established in the cerebral meninges. In order to examine whether the function of AKAP12 in the property transition of epithelial cells is cell-specific, two types of epithelial cells with different origins were used. The retina is a central nerve organ which shares the same developmental origin with the brain. Because the retina is similar to the brain in terms of structure and property, the retinal epithelial cell ARPE19 was employed.

The A549 cell line, derived from the bronchial epithelium, retains the properties of the epithelium and is widely used for EMT. When the expression of AKAP12 was suppressed, the epithelial cell markers occludin, E-cadherin and ZO-1 were decreased in expression level whereas the expression of α-SMA, a marker characteristic of mesenchymal cells, increased. The data indicate that the suppression of AKAP12 expression induces EMT (Epithelial Mesenchymal Transition) (see FIG. 12).

In this regard, an examination was made of the expression of main transcription regulators which are involved in EMT. The expression of SNAI1 was found to be significantly regulated by AKAP12 (see FIG. 13).

Various fields are studying SNAI1, an EMT factor which plays an important role in the developmental process and cancer metastasis. To examine whether SNAI1 participates directly in the EMT triggered by the down-regulation of AKAP12, the expression of both AKAP12 and SNAI1 were down-regulated. As a result, EMT was suppressed (see FIG. 14).

In addition, important signaling pathways were examined to ascertain the regulation of SNAI1 by AKAP12. The down-regulation of AKAP12 led to the phosphorylation of the proteins in the PKC (Protein Kinase C)~C-raf~MEK (mitogen activated kinase)~P38 pathway. To verify the direct connection of this pathway with the up-regulation of SNAI1, respective specific regulators were used. As a result, the transcription level of SNAI1 increased by the down-regulation of AKAP12 recovered back up to the normal level (see FIG. 15).

Figure 17:
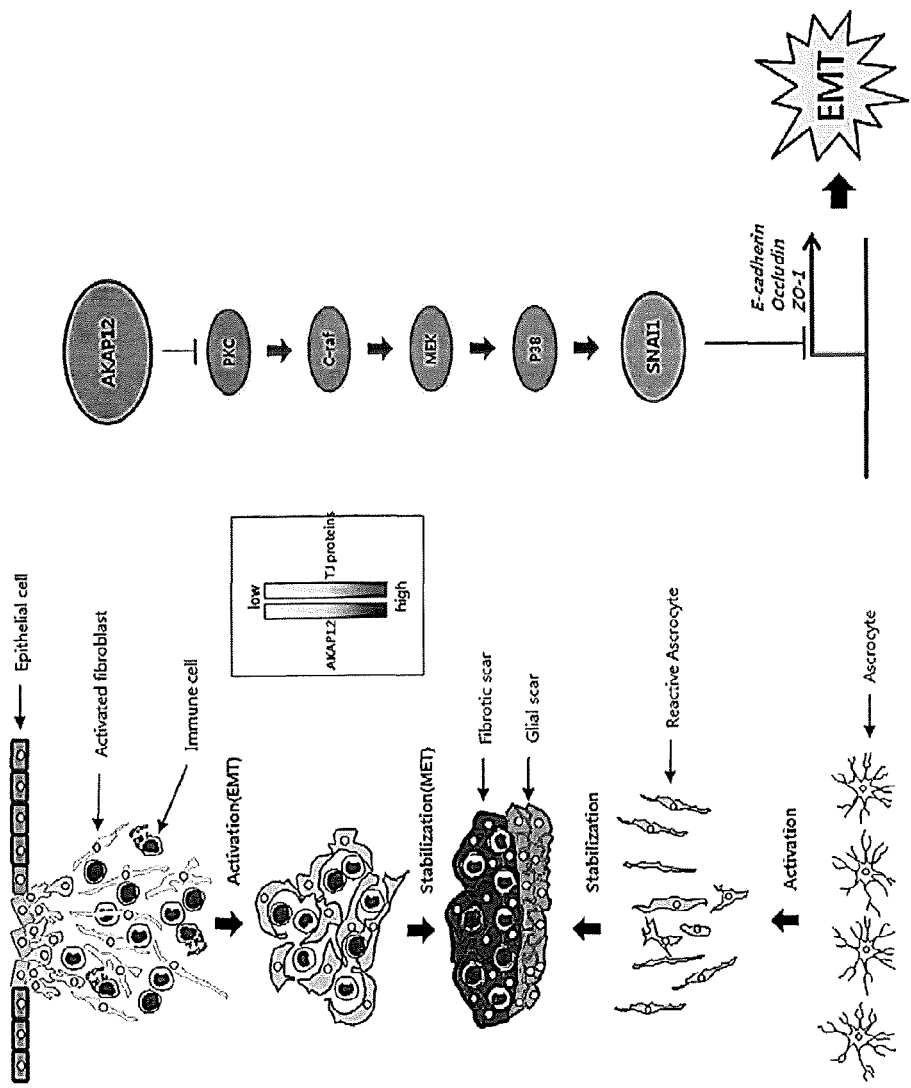
FIG. 17 is a schematic view showing the mechanism of AKAP12 activity in the establishment of a fibrotic-glial scar.

To sum up, when an injury is generated around the cerebral meninges of the central nervous system, an inflammation signal induces the stable cells of epithelial properties, which accounts for a predominant portion of the cerebral meninges, to decrease their expression level of AKAP12, which activates the PKC~C-raf~MEK~P38 signaling pathway, normally suppressed by AKAP12, leading to SNAI1-induced EMT. The cerebral meninges-derived fibroblasts converted from the epithelial cells of the cerebral meninges infiltrate into the tissue, forming a loose scaffold capping the inflammatory region. Thereafter, when the inflammation tapers off or the expression of AKAP12 is recovered by a signal, the PKC~C-raf~MEK~P38~SNAI1 signaling pathway is deactivated. As the expression of SNAI1 is down-regulated, the expression of junction proteins, such as occludin, E-cadherin, and ZO-1, which is suppressed by SNAI1 is recovered, thus completing the function of fibrotic scars as a physiological barrier. Likewise, glial scars are formed into a physiological barrier. According to a similar mechanism, the junction proteins such as occludin, E-cadherin and ZO-1 are increased in expression level with increasing AKAP12 expression around the inflamed region, thus making glial scars completely function as a physiological barrier (see FIG. 17).

From the results, it is clearly appreciated that AKAP12 controls the activity and motility of fibroblasts and astrocytes, two major components of fibrotic-glial scars, and plays an important role in the formation of fibrotic-glial scars. Hence, the formation of fibrotic-glial scars can be controlled by regulating the expression or activity of AKAP12, which is ultimately expected to treat central nervous system diseases or to improve the prognosis thereof.

Therefore, the present invention provides a method for treating central nervous system diseases. The method comprises administering an expression or activity regulator of AKAP12 to a subject in need of the treatment. In an embodiment, the method may further comprise administering an anti-inflammatory agent to the subject. Examples of the central nervous system diseases include stroke, post-traumatic stress syndrome, and spinal injury.

No limitations are imparted to the administration of the expression or activity regulator of AKAP12. For example, this regulator may be administered orally, intraarterially, intravenously, trandermally, intranasally, transbronchially, or intramuscularly. In addition, it is clearly understood to those skilled in the art that the dosage of the expression or activity regulator of AKAP 12 may vary depending on various factors including patient's weight, age, gender and health condition, diet, the time of administration, the route of administration, the rate of excretion, the severity of disease, and the like.

The pharmaceutical composition of the present invention may further comprise a pharmaceutically acceptable carrier. Examples of the pharmaceutically acceptable carrier include saline, sterile water, Ringer's solution, buffered saline, dextrose solutions, maltodextrin solutions, glycerol and ethanol. The pharmaceutical composition of the present invention may be formulated into typical dosage forms, with the aid of pharmaceutically acceptable diluents or excipients.

Mode for the Invention

A better understanding of the present invention may be obtained through the following examples which are set forth to illustrate, but are not to be construed as limiting the present invention.

EXAMPLES

Example 1

Expression of AKAP12 in the Formation Process of Fibrotic-Glial Scars

After local injuries were introduced into the cerebral tissues thereof, photothrobosis mouse models were monitored for the formation of fibrotic-glial scars and the expression of AKAP12 over time.

In detail, an anesthetized C57BL6 mouse was injected with 100 µL of the stain rose Bengal (10 mg/ml) via the caudal vein, followed by incising the head skin. Photothrombosis was induced at a 1 mm-diameter head region located 1.5 mm posterior and 2.5 mm right from the bregma with illumination of light for 20 min. In response to the light, the stain generated free radicals which induced the formation of a thrombus, thus injuring the tissue. After the lapse of a given time, the models were perfused with physiological saline to remove blood from the stained tissues, and the brain was excised and fixed in 4% PFA. The fixed cerebral tissue was dehydrated and dissected to prepare OCT blocks which were then cryosectioned into slices 30 µm thick and kept in a storage buffer. The tissues were immunostained with antibodies specific for proteins of interest, followed by visualization of the proteins under a fluorescence microscope and a multifocal fluorescence microscope.

As seen in FIG. 1, cerebral meninges-derived fibroblasts and cerebral astrocytes, which both are the main constitutional cells of fibrotic glial scars, migrated into inflammatory tissue with the lapse of time to form two separate layers which isolated the inflammation tissue from surrounding cerebral tissues. In this scaffold, AKAP12 was expressed at a high level.

After being dissected elaborately, the fibrotic-glial scar tissue was subjected to Western blotting.

In detail, mice were sacrificed by cervical dislocation, followed by excision of the brain. The brain was loaded on a dissection frame and dissected with a microtome to obtain only lesion regions. The dissected tissues were homogenized in a solution and centrifuged to isolate proteins. Protein analysis was done with Western blotting. Four mice were employed for each condition and the results of Western blotting were quantitatively analyzed using an image) program (see FIG. 2).

Figure 2:
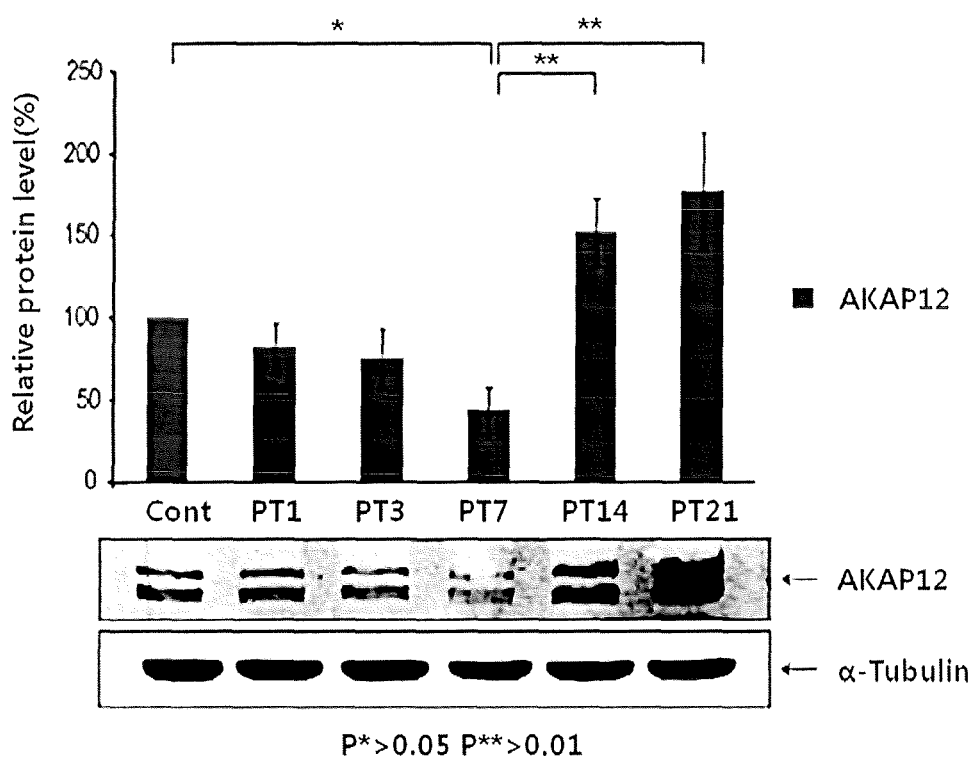
FIG. 2 shows expression levels of AKAP12 in a cerebral lesion with time after cerebral injury: the brain was excised 1, 3, 7, 14 and 21 days after cerebral injury and dissected to obtain only a fibrotic-glial scar portion from which proteins were extracted.

As is understood from the data of FIG. 2, the expression level of AKAP12 was decreased in the early stage wherein inflammation was intensified and the main constitutional cells of fibrotic-glial scar migrated in response to the inflammation signal (PT1 to PT7), but was increased in the late stage wherein the scaffold of fibrotic-glial scar became sturdy (PT14 to PT21).

To identify the constitutional cells of fibrotic-glial scar which express AKAP12, AKAP12 and a marker characteristic of each cell were double stained.

On Day 7 after tissue injury, a sample was prepared for histostaining and washed three times with PBS. The sample was incubated overnight at 4° C. with respective antibodies against AKAP12, CD45, fibronectin and ERTR7 in PBS containing BSA, TritonX-100 and FBS. The sample was washed three times with PBS, incubated at room temperature for 1 hr with a fluorescence-conjugated secondary antibody, and washed again three times with PBS, followed by visualizing the sample loaded on slides using a fluorescence microscope (see FIG. 3).

Figure 3:
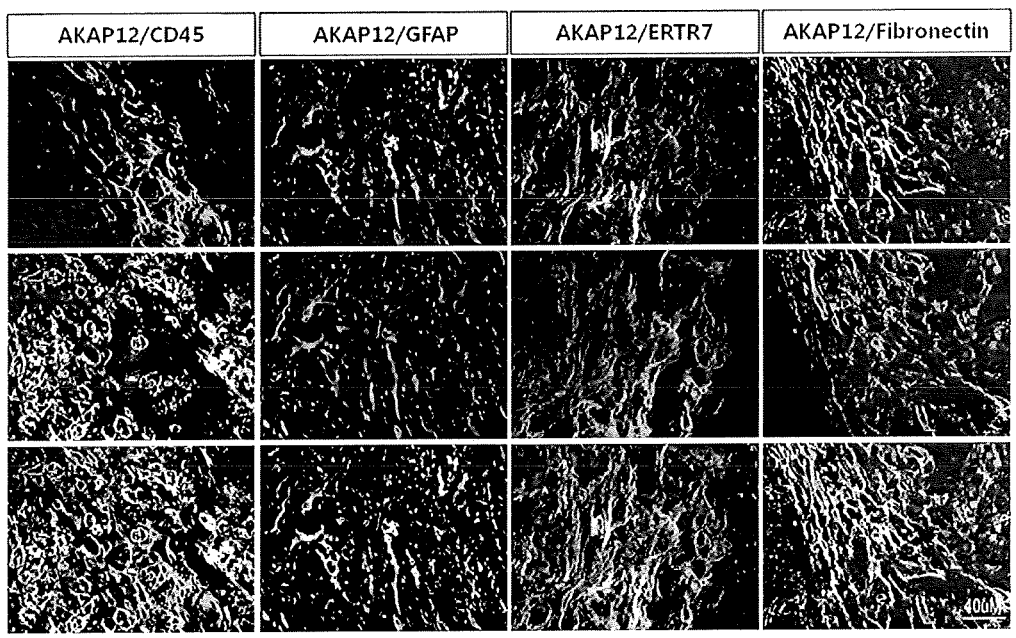
FIG. 3 is of fluorescence photographs indicating the cells expressing AKAP12 among various constitutional cells of the fibrotic-glial scar after they were immunostained with cell-specific markers.

As shown in FIG. 3, AKAP12 was expressed predominantly in cerebral meninges-derived fibroblasts and cerebral astrocytes, but only slightly in immune cells.

AKAP12 was further analyzed for expression pattern according to the time of formation of the fibrotic-glial scar.

A sample was prepared for histostaining and washed three times with PBS. The sample was incubated overnight at 4° C. with respective antibodies against AKAP12, α-SMA, fibronectin and GFAP in PBS containing BSA, TritonX-100 and FBS. The sample was washed three times with PBS, incubated at room temperature for 1 hr with a fluorescence-conjugated secondary antibody, and washed again three times with PBS, followed by visualizing the expression patterns of AKAP12 in the sample loaded on slides using a fluorescence microscope. The results are given in FIG. 4 [GFAP: astrocyte marker, FN (fibronectin): fibroblast marker, α-SMA: activated fibroblast].

Figure 4:
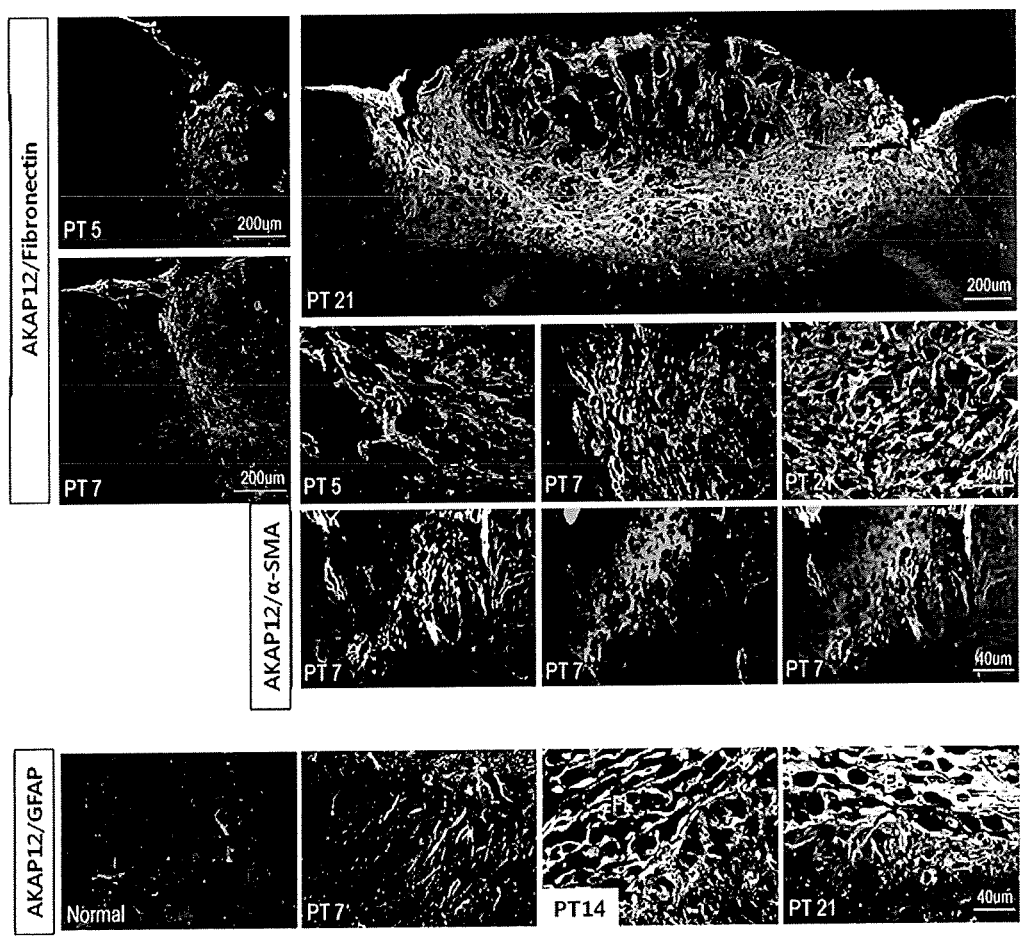
FIG. 4 is of fluorescence photographs showing that the expression of AKAP12 increases with the stabilization of cerebral meninges-derived fibroblasts and also increases as reactive astrocytes form interconnections with each other to establish a stable scaffold as a barrier.

As seen in FIG. 4, although a number of cerebral meninges-derived fibroblasts infiltrated into the inflammation tissue at the time of PT5, the expression of AKAP12 was observed in only a small number of the cells. At PT21 when the scar scaffold was completed, however, almost all the fibroblasts were observed to express AKAP12.

From the data, it can be understood that the expression level of AKAP12 in cerebral meninges cells in a stable state is decreased by an inflammation signal and thus become actively motile so that they are apt to infiltrate into the cerebral tissue and that as the cells recover the expression level of AKAP12, they are stabilized, with the scaffold of the scar being completed.

Likewise, normal astrocytes expressed very low levels of AKAP12, but reactive astrocytes, which are activated by an inflammation signal, were observed to increase in the expression level of AKAP12 and migrate into the inflamed region. A peak of AKAP12 expression was detected in the reaction astrocytes which were entangled with each other to form a complete scar. Astrocytes are a sub-type of glial cell in the central nervous system and play an important role in maintaining the homeostasis of the brain. Astrocytes in a normal state extend axons in a radiant pattern to form star shapes. In response to an inflammation signal or a tissue injury, astrocytes are activated to actively proliferate and are transfigured into indeterminate forms which can readily migrate. The activated astrocytes are called reactive astrocytes.

Example 2

Role of AKAP12 in the Establishment of Fibrotic-Glial Scars as a Physiological Barrier The results of Example 1 imply a correlation of AKAP12 with the function of fibrotic-glial scars. The following experiment was done to ascertain the correlation.

Figure 5:
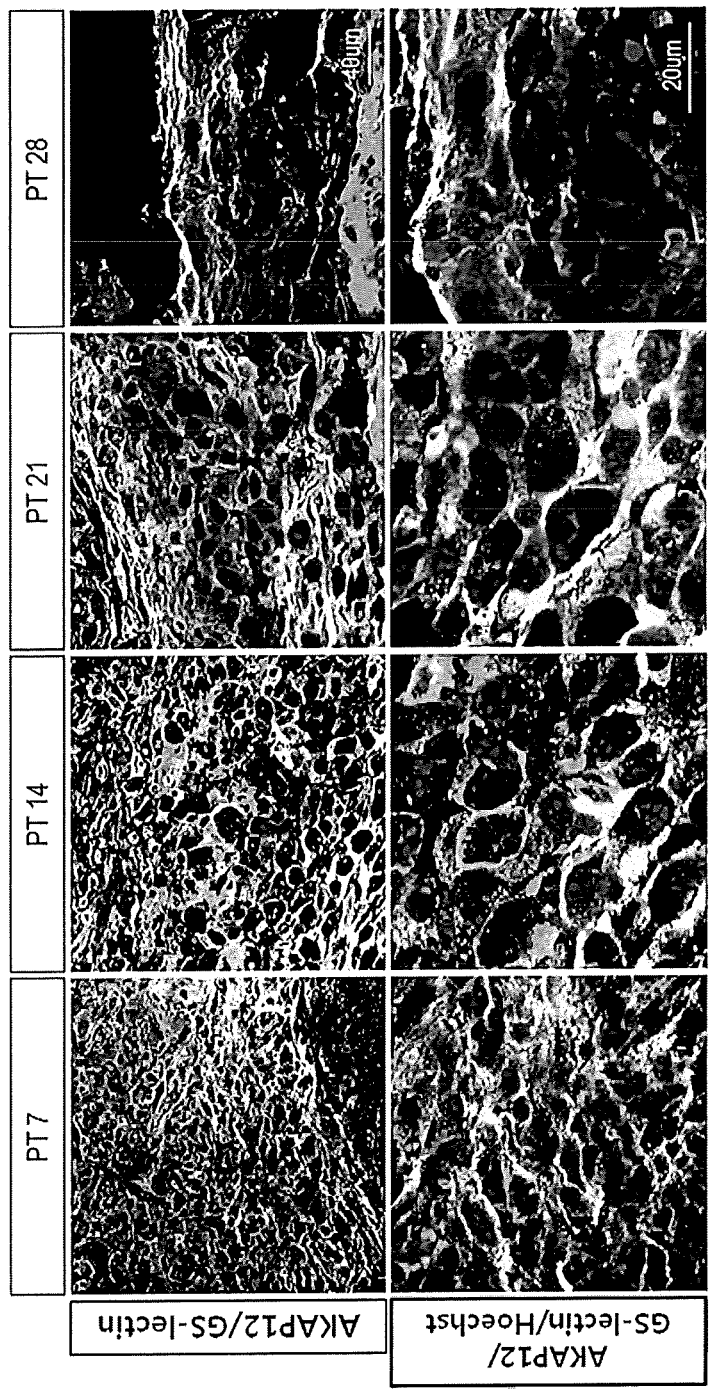
FIG. 5 is of fluorescence photographs showing that the fibrotic scar of AKAP12-expression fibroblasts is not simply a scaffold, but functions as a barrier that caps and isolates inflammatory cells.

FIG. 5 are of photographs after histofluorescence staining [GS-lectin: inflammatory cell staining, Hochest(Blue): nucleus staining].

A sample was prepared for histostaining and washed three times with PBS. The sample was incubated overnight at 4° C. with an antibody against AKAP12 in PBS containing BSA, TritonX-100 and FBS. The sample was washed three times with PBS, incubated at room temperature for 1 hr with a fluorescence-conjugated secondary antibody in a GS-lectin solution, and washed again three times with PBS, followed by visualizing the expression patterns of AKAP12 in the sample loaded on slides using a fluorescence microscope.

As seen in FIG. 5, the cerebral meninges-derived fibroblasts which expressed AKAP12 did not become tangled to form a simple layer structure, but were inter-connected with each other to cap the inflammatory cells and prevent them from infiltrating into the tissue.

FIG. 6 is a graph showing tissue Western blotting results of the scar.

The brain was elaborately dissected to obtain only the fibrotic glial scar from which proteins were then extracted. Expression patterns were quantitatively analyzed by Western blotting and the results are depicted in FIG. 6.

As is apparent from the date of FIG. 6, occludin, E-cadherin and ZO-1, which all function to create the junction between cells and thereby establish the scar as a physical barrier, were expressed in a pattern similar to that of AKAP12.

Until one week after tissue injury during which inflammation was intensified, the expression levels in the cerebral meninges of occludin, E-cadherin and ZO-1 were decreased by an inflammation signal, with the concomitant occurrence of EMT. At the time of week two or three after tissue injury, the expression levels of occludin, E-cadherin and ZO-1 increased with the stabilization of the newly formed fibrotic-glial scar. As for α-SMA, its expression was increased in both activated fibroblasts and astrocytes. Thus, α-SMA was used as a marker for indicating activation, and expressed in a pattern that was the reverse of that of occludin, E-cadherin or ZO-1. In consideration of the expression pattern of AKAP12 which is similar to that of occludin, E-cadherin and ZO-1, but the reverse of that of α-SMA, the down-regulation of AKAP12 by inflammation could induce EMT while the expression of AKAP12 would be increased with a reduction in the inflammation, contributing to the stabilization of fibrotic-glial scars.

Coinciding with the Western blotting, immunofluorescence staining showed that occludin, E-cadherin and ZO-1, which are all responsible for cell to cell junctions, were expressed in cerebral meninges-derived fibroblasts (FIG. 7) and reactive astrocytes (FIG. 8), both of which overexpress AKAP12 (FL: cerebral meninges-derived fibroblast layer, Reactive astrocyte(GFAP(+)).

An Evans blue extravasation assay was performed to ascertain the function of the fibrotic-glial scar as a physiological barrier.

The damage of the blood brain barrier, which serves to protect the brain from external toxic materials, can be examined using the Evans blue extravasation assay.

An injury was induced in cerebral tissue using a PT model. After a given time, Evans blue dye was injected into the heart of the mouse model and allowed to circulate through the body for two hours to penetrate into the tissue. The Evans blue dye was removed from blood by perfusion with PBS (phosphate buffered saline), with blue appearances only at regions in which the blood brain barrier had collapsed (see FIG. 9).

As seen in FIG. 9, the inflammation which intensified at the time of PT 1-7 during the fibrotic-glial scar was being formed, collapsed the blood brain barrier over a region wider than the PT-induced injured site, so that the Evans blue dye infiltrated into the tissues of the region. In contrast, inflammation-induced secondary injury was nearly perfectly suppressed at the time of PT 14-21 when the establishment of the fibrotic-glial scar was completed.

A comparison of the degree of formation of fibrotic-glial scar in wild-type and AKAP12-knockout mice was carried out to examine the function AKAP12 has in the formation of fibrotic-glial scarring.

Figure 10:
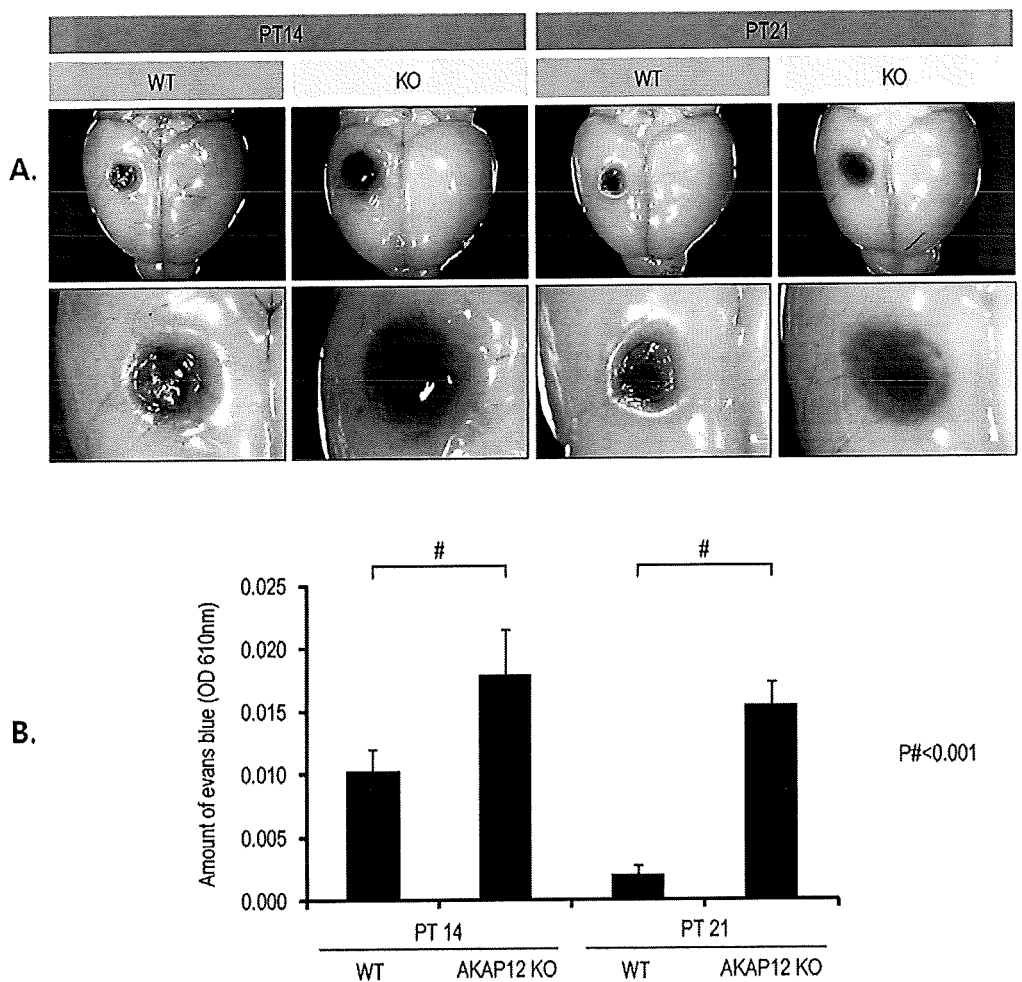
FIG. 10, comprising

An Evans blue extravasation assay was performed at the time of PT 21 when the fibrotic-glial scar was completely established, and the results are given in FIG. 10.

As seen in FIG. 10, compared to the WT mice, the Evans blue dye infiltrated into regions that were wider in the KO mice. This result indicates that the blood brain barrier had collapsed allowing inflammatory materials or cells to leak into tissues around the fibrotic-glial scar. That is, the establishment of the fibrotic-glial scar in the AKAP12-KO mice was problematic.

A TCC (triphenyltetrazolium chloride) staining assay was done and the results are given in FIG. 11.

After being excised as quickly as possible, the brain was sectioned to a thickness of 1 mm. The brain sections were incubated at 37° C. for 20 min in a TTC solution, fixed with 4% paraformaldehyde, and photographed. The percentage of non-stained volumes (infarct volumes) to the total brain volume was calculated. A tetrazolium salt is enzymatically reduced to red compounds in the living tissues due to the activity of various dehydrogenases. In contrast, it remains as white TTC in dead tissues. An examination was made of the role of AKAP12 in the establishment of fibrotic-glial scars which act as a physiological barrier. In this regard, the brains of wild-type and AKAP12-knockout mice were injured. After 21 days passed during which a fibrotic-glial scar had been functionally completed, a TTC staining assay was performed. A relatively increased white volume in the AKAP12-knockout mice reflects an increased tissue injury, indicating that the fibrotic-glial scar was functioning abnormally.

As seen in FIG. 11, the tissue infarct volume of the KO mice was about twice as large as that of the wild-type mice.

Taken together, the data obtained from the in vivo experiments demonstrate that AKAP12 regulates the activity and motility of the two main constitutional cells of fibrotic-glial scar, fibroblasts and astrocytes, and plays an important role in the formation of a fibrotic-glial scar. Hence, the formation of fibrotic-glial scars can be controlled by regulating the expression or activity of AKAP12, which is ultimately expected to treat central nervous system diseases or to improve the prognosis thereof.

Example 3

Examination on the Mechanism of AKAP12 Activity in the Establishment of Fibrotic-Glial Scar To reveal the mechanism of AKAP12 activity in the formation of fibrotic-glial scars, immunofluorescence staining and Western blotting assays were conducted in vitro as follows, and the results are given in FIG. 12.

Immunofluorescence Staining Assay

Cells were loaded on circular cover glass and incubated overnight. Using oligofectamine (Invitrogen), control Si or AKAP12 Si, which induces the degradation of mRNA of AKAP12, was introduced into the cells which were then incubated for 48 hrs. They were fixed by treatment with 100% ethanol (4° C.) for 40 min and then with 100% acetone (room temperature) for 3 min. After their membranes became permeable in 0.05% tritonX-100 PBS, the cells were treated with a blocking solution to block non-specific antibodies from binding thereto. The cells were incubated overnight at 4° C. with 1:300-diluted antibodies against ZO-1 and occludin and washed. Following incubation with a 1:1000 dilution of a secondary antibody at room temperature, the cells were washed and observed on slides under a fluorescence microscope.

Western Blotting

With the aid of oligofectamine (Invitrogen), control Si or two types of AKAP12 Si (#1 si, #2 si), that induce the degradation of AKAP12 mRNA, were transfected into ARPE-19 and A549 cells which were then incubated for 48 hrs. The cells were washed with PBS before protein extraction therefrom. The proteins were arranged on gel according to size by electrophoresis, and transferred onto a membrane. After treatment with a blocking buffer to prevent the binding of non-specific antibodies, the membrane was incubated overnight at 4° C. with specific antibodies and washed. Treatment with a 1:3000 dilution of secondary antibody at room temperature was followed by washing. The proteins were visualized for analysis.

From the data of FIG. 12, it can be understood that when the expression of AKAP12 is down-regulated therein, ARPE-19 and A549, which both are epithelial cells, decrease in the expression level of the epithelial cell markers occludin, E-cadherin and ZO-1, but increase in the expression level of α-SMA, a marker for activated mesenchymal cells. This result indicates that the down-regulation of AKAP12 induces EMT (Epithelial Mesenchymal Transition).

Of the factors of FIG. 12, the expression regulation of SNAI1 by AKAP12 was examined.

Various fields are studying SNAI1, an EMT regulator which plays an important role in the developmental process and cancer metastasis. To examine whether SNAI1 participates directly in the EMT triggered by the down-regulation of AKAP12, an immunofluorescence assay and Western blotting were performed, and the results are given in FIG. 13.

Figure 13:
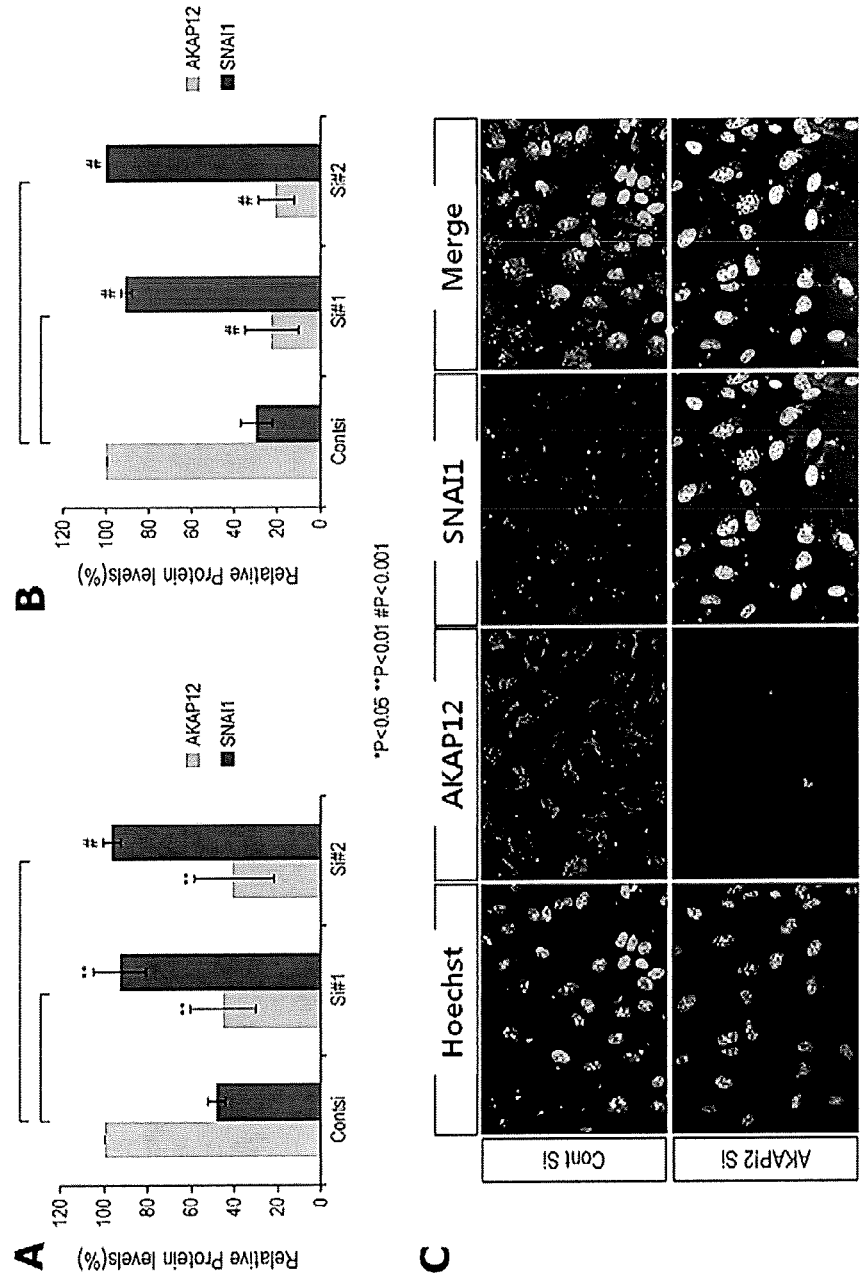
FIG. 13, comprising

As is apparent from the data of FIG. 13, the expression of SNAI1 was significantly regulated by AKAP12.

It was confirmed by the experiments that the down-regulation of AKAP12 increased the expression of SNAI1 and triggered EMT, which is coincident with previous reports that SNI1 induces EMT. Based on the data, it can be inferred that the EMT triggered by the down-regulation of AKAP12 would be mediated by SNAI1.

To examine whether the EMT triggered by the down-regulation of AKAP12 is suppressed upon the down-regulation of SNAI1, the expression of both AKAP12 and SNAI1 were treated with si.

The final concentration of si in each batch was adjusted to 100 nM by using control si 100 nM for Lane 1 CsiCsi, control si 50 nM plus AKAP12 si 50 nM for Lane 2 CsiAsi, control si 50 nM plus SNAI1 si 50 nM for Lane 3 SsiCsi, and SNAI1 si 50 nM plus AKAP12 si 50 nM for Lane 4 SsiAsi. Cells were transfected with Si using Oligofectamine (Invitrogen), and then incubated for 48 hrs. Following washing the cells, proteins were extracted from the cells using lysis buffer and arranged on a gel plate according to size. The proteins were transferred from the gel to a membrane which was then treated with blocking buffer to prevent non-specific antibodies from binding thereto. The membrane was incubated overnight at 4° C. with respective antibodies and washed. Treatment with a 1:3000 dilution of a secondary antibody was followed by washing with PBS. The proteins were visualized for analysis. The experiment was performed in triplicate. The measurements were quantitatively analyzed using an image) program, and the results are shown in FIG. 14.

Figure 14:
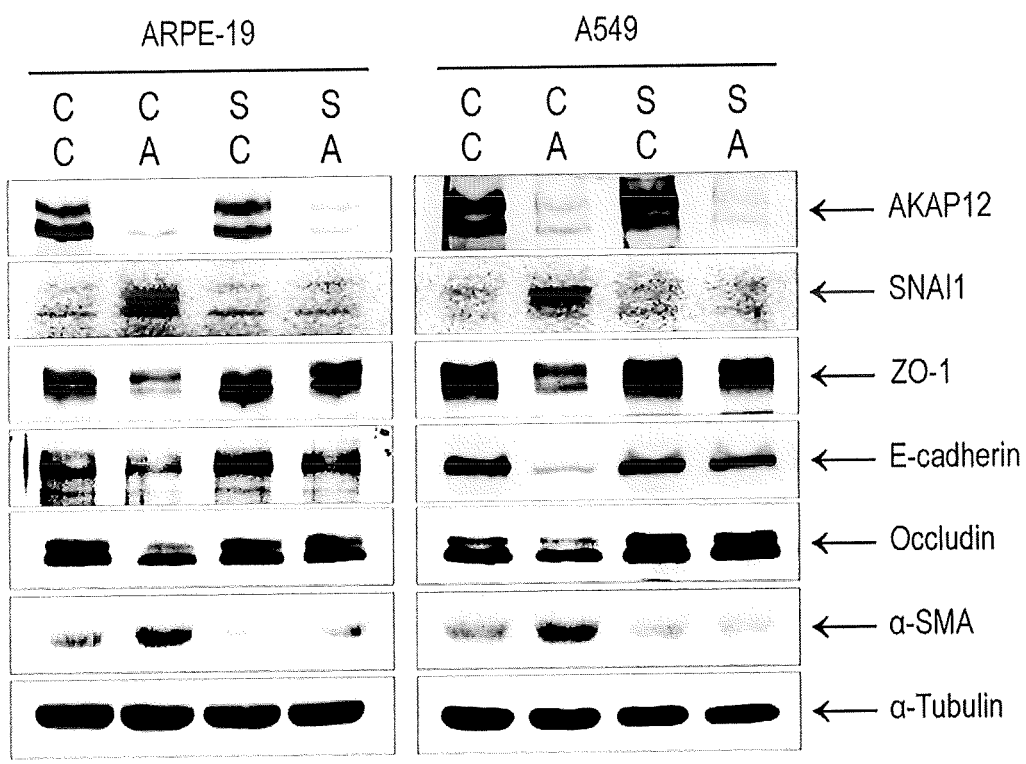
FIG. 14 shows the role of SNAI1 as a downstream regulator in the activation caused by the down-regulation of AKAP12.

In spite of the down-regulation of AKAP12, as seen in FIG. 14, the down-regulation of SNAI1 suppressed EMT.

The AKAP12-induced SNAI1 regulation was further examined by the following experiment.

ARPE-19 cells were transfected with control Si or AKAP12 Si, which induces the degeneration of AKAP12 mRNA, with the aid of Oligofectamine (Invitrogen), and then were incubated for 48 hrs. Because a phosphorylation signal is not detected under normal conditions, it was amplified by incubating the cells for 30 min with the signal inducer TPA (200 nM). The cells were washed. Proteins were extracted from the cells using lysis buffer and arranged on a gel plate according to size by electrophoresis. The proteins were transferred from the gel to a membrane which was then treated with blocking buffer to prevent non-specific antibodies from binding thereto. The membrane was incubated overnight at 4° C. with respective antibodies and washed. Treatment with a 1:3000 dilution of a secondary antibody was followed by washing with PBS. The proteins were visualized for analysis. The results are given in FIG. 15.

Figure 15:
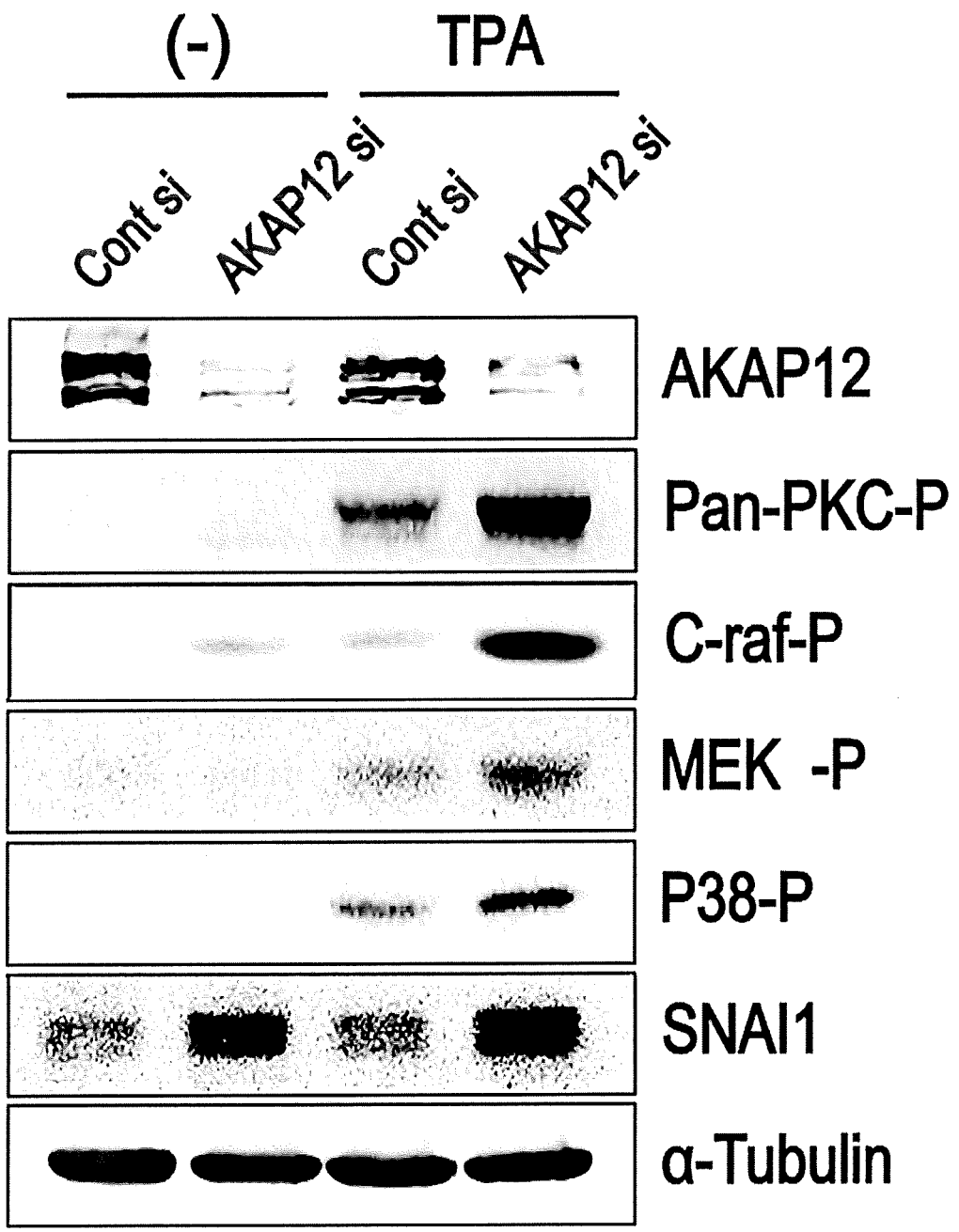
FIG. 15 shows the activation of the PKC~C-raf~MEK~p38 signaling pathway upon the down-regulation of AKAP12.

As seen in FIG. 15, the down-regulation of AKAP12 led to the phosphorylation of the proteins in the PKC (Protein Kinase C)~C-raf~MEK (mitogen activated kinase)~P38 pathway.

To verify the direct connection of this pathway with the up-regulation of SNAI1, respective specific regulators were used.

In this context, ARPE-19 cells were transfected with control Si and AKAP12 Si, which induces the degeneration of AKAP12 mRNA, with the aid of Oligofectamine (Invitrogen) and were incubated for 24 hrs, followed by treatment with respective signal inhibitors for 24 hrs. The cells were washed with PBS and lysed with lysis buffer to extract proteins. They were arranged on a gel plate according to size by electrophoresis and transferred from the gel to a membrane. The membrane was treated with a blocking solution to prevent non-specific antibodies from binding thereto and was incubated overnight at 4° C. with respective antibodies. The membrane was washed with PBS, followed by treatment with a 1:3000 dilution of a secondary antibody at room temperature. The proteins were visualized for analysis. The results are given in FIG. 16 [DMSO: reagents dissolved, GF109203X(5 uM): PKC inhibitor, U0126(10 uM):MEK1/2inhibitor, Bay43-9006(1 uM):Raf-1 inhibitor, SB203580(10 uM):p38 inhibitor].

Figure 16:
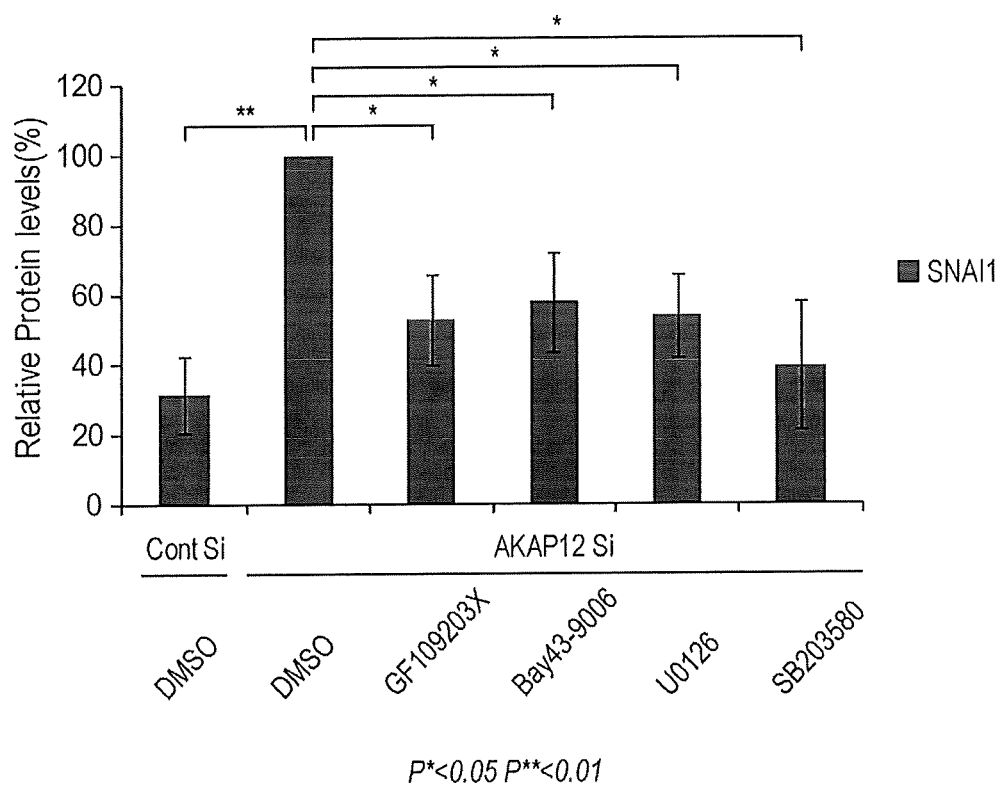
FIG. 16 shows the disappearance of the effect of AKAP12 on SNAI1 upon treatment with inhibitors of the PKC~C-raf~MEK~p38 signaling pathway.

As is apparent from the data of FIG. 16, the transcription level of SNAI1 increased by the down-regulation of AKAP12 had recovered to normal levels.

Taken together, the data obtained in the Examples demonstrate that when an injury is generated around the cerebral meninges of the central nervous system, an inflammation signal induces the epithelial properties of stable cells, which accounts for a predominant portion of the cerebral meninges, to decrease in the expression level of AKAP12, which activates the PKC~C-raf~MEK~P38 signaling pathway normally suppressed by AKAP12, leading to SNAI1-induced EMT. The cerebral meninges-derived fibroblasts converted from the epithelial cells of the cerebral meninges infiltrate into the tissue, forming a loose scaffold which caps the inflammatory region. Thereafter, when the inflammation tapers off or the expression of AKAP12 is recovered by a signal, the PKC~C-raf~MEK~P38~SNAI1 signaling pathway is deactivated. As the expression of SNAI1 is down-regulated, the expression of junction proteins, such as occludin, E-cadherin, and ZO-1, which is suppressed by SNAI1 is recovered, thus completing the function of fibrotic scars which act as a physiological barrier. Likewise, glial scars form a physiological barrier. According to a similar mechanism, the expression levels of junction proteins such as occludin, E-cadherin and ZO-1 are increased with increasing of AKAP12 expression around the inflamed region, thus making glial scars completely function as a physiological barrier (see FIG. 17).

Example 4

Examination on Regulatory Mechanism of AKAP12

The results obtained above demonstrated the induction of EMT by downregulation of AKAP12. In order to ascertain a regulator upstream of AKAP2, ARPE-19 cells were incubated for 24 hours in a serum-free medium and then for an additional 48 hours with TGF-$\beta$1 (10 ng/mL) and RA (10 $\mu$M), followed by quantification of AKAP12. The results are shown in FIG. 18.

Figure 18:
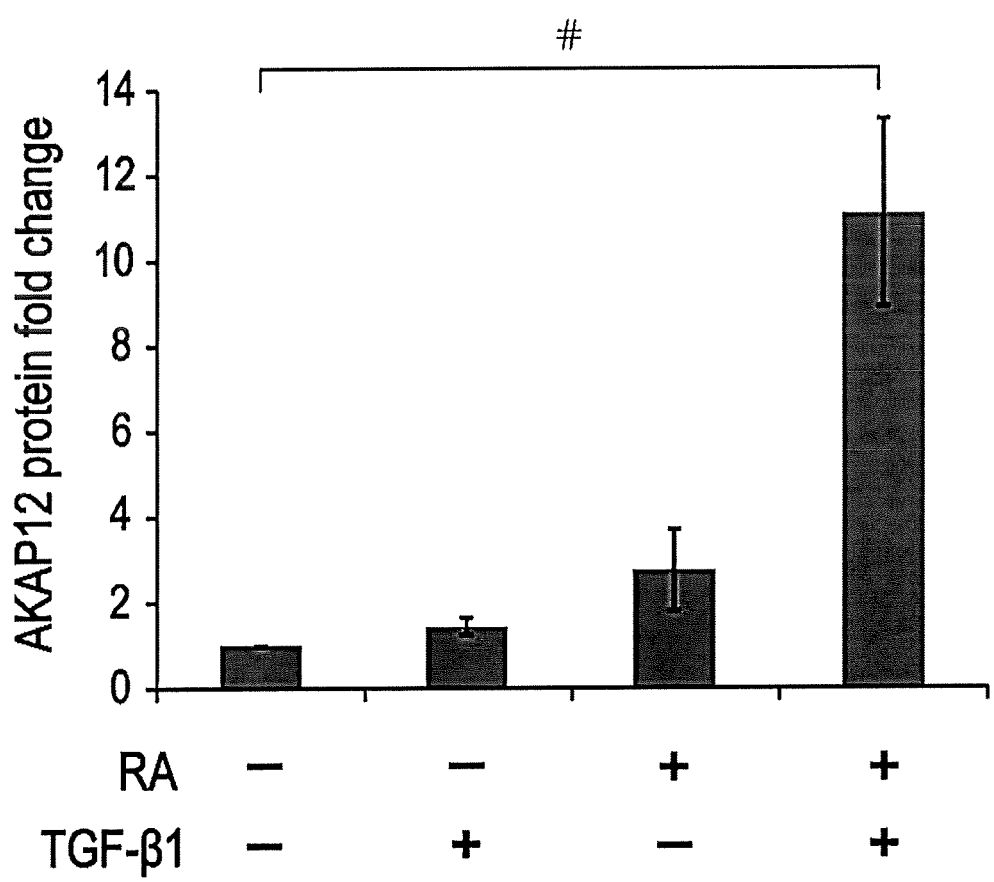
FIG. 18 shows an increase in AKAP12 expression upon concomitant treatment with RA and TGF-$\beta$1.

As can be seen in FIG. 18, the expression of AKAP12 was significantly increased upon concomitant treatment with TGF-$\beta$1 and RA (Retinoic acid), compared with treatment with none of them or one in isolation.

Figure 19:
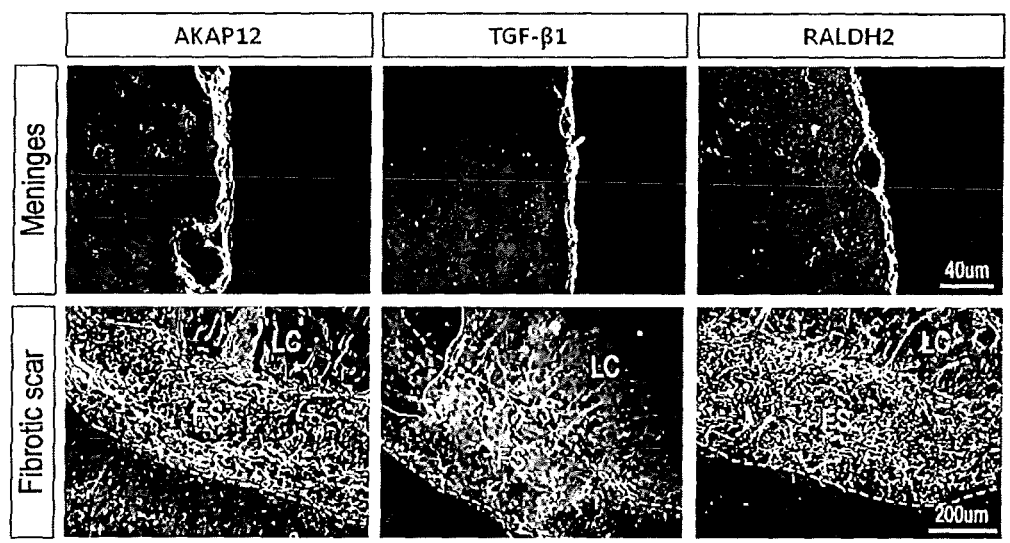
FIG. 19 shows the expression of AKAP12, TGF-$\beta$1, and RALDH2 occurring at the same regions in both the cerebral meninges and the fibrotic scars.

In addition, day 21 after cerebral injury, the brain tissues of the mice were subjected to histoimmunostaining with antibodies specific for AKAP12, TGF-$\beta$1, and RALDH2. As seen in FIG. 19, AKAP12 was expressed in the same regions of the cerebral meninges and the fibrotic scar as were TGF-$\beta$1 and retinaldehyde dehydrogenase 2 (RALDH2), an enzyme for producing RA. Also, the cerebral meninges allows for a high level of expression of TGF-$\beta$1, a main trigger of EMT, in spite of having the epithelial characteristic of separating the central nervous system from the external environment (see FIG. 19).

To examine the effect of RA and TGF-$\beta$1 on EMT, ARPE-19 cells were cultured for 24 hours in a serum-free medium and then for an additional 48 hours with TGF-$\beta$1 (10 ng/mL) and RA (10 $\mu$M), followed by Western blotting for AKAP12 and EMT markers. The results are shown in FIG. 20.

Figure 20:
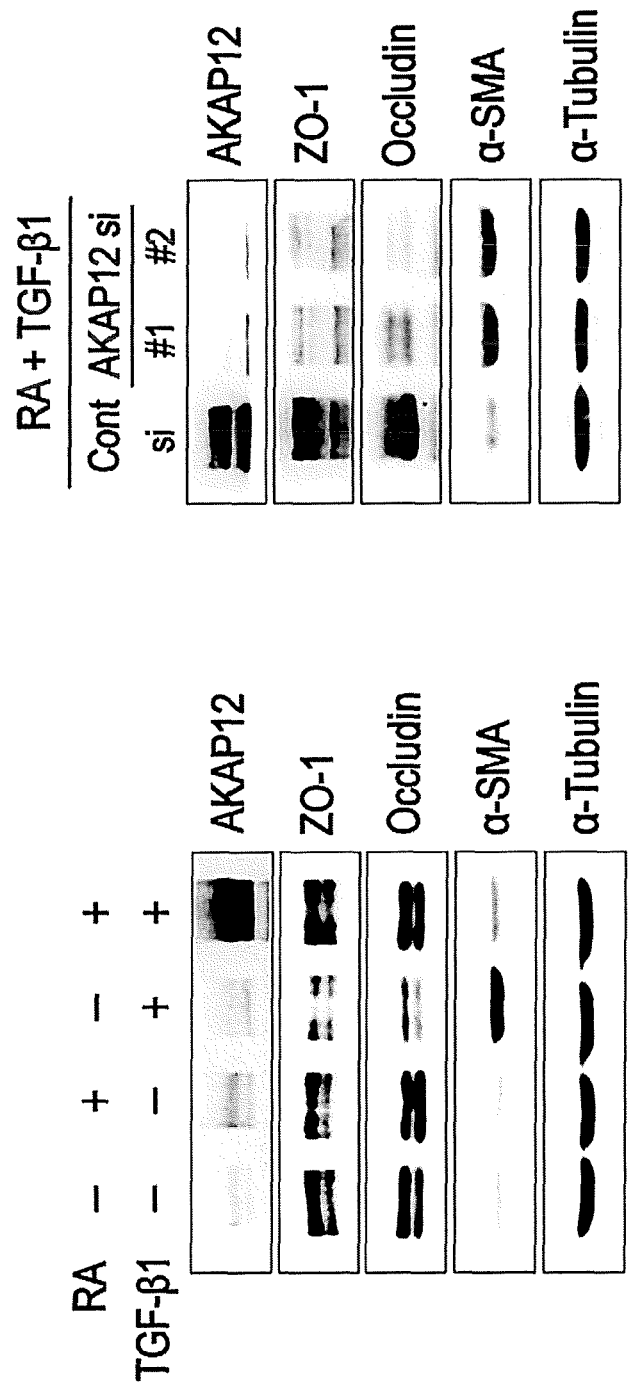
FIG. 20 shows that RA can suppress TGF-$\beta$1-induced EMT, but cannot in the absence of AKAP12.

As can be seen in FIG. 20, co-treatment with RA and TGF-$\beta$1 suppressed TGF-$\beta$1-induced EMT whereas RA cannot suppress EMT in the absence of AKAP12.

Figure 21:
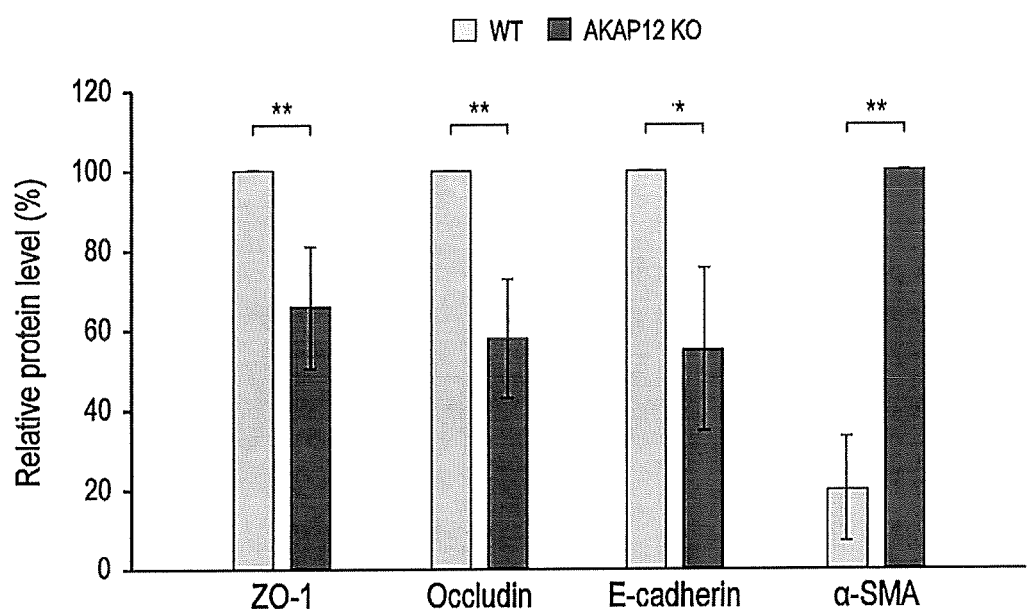
FIG. 21 shows an EMT increase in AKAP12-knockout mice.
Figure 22:
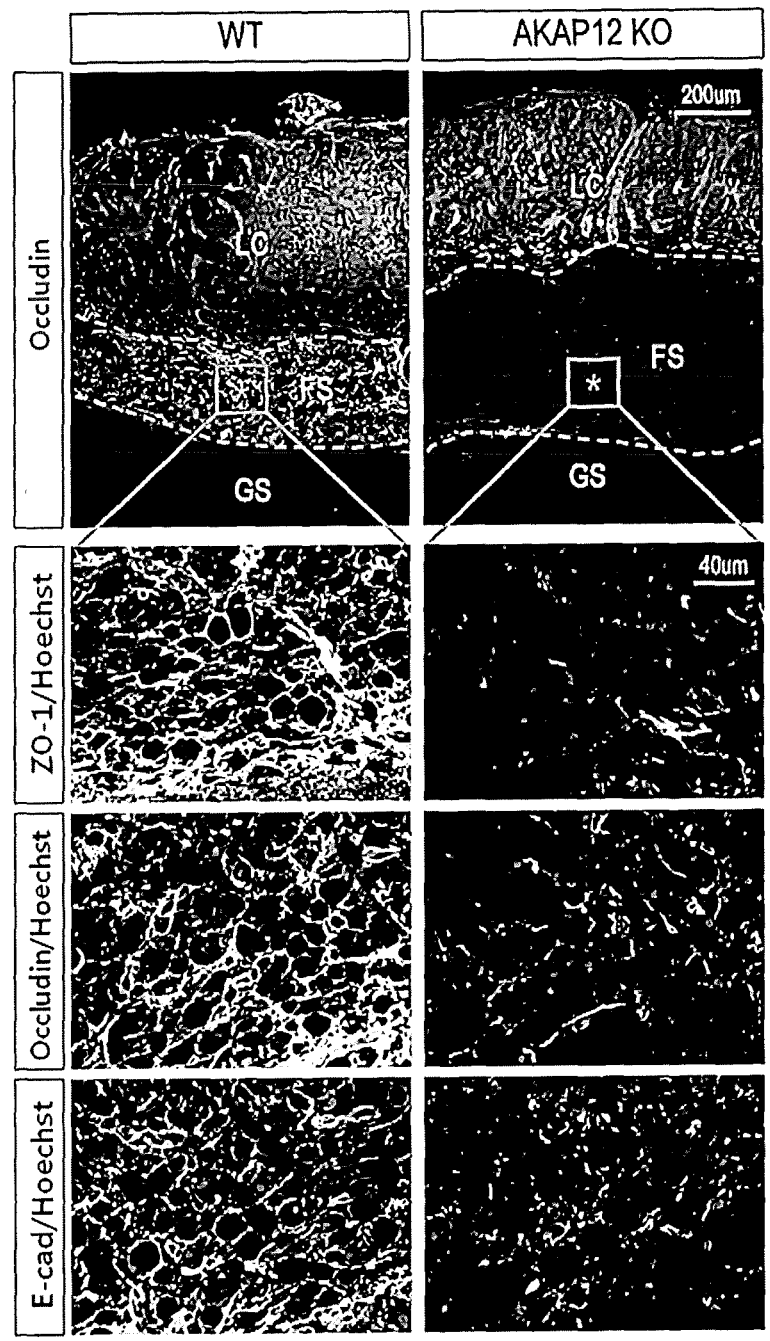
FIG. 22 shows that the epithelial markers decrease in expression in AKAP12-knockout mice from 21 days after injury.

Further, on day 21 after cerebral injury, the brains were excised from normal and AKAP12-knockout mice and the fibrotic scar tissues was elaborately cut out, so that the expression of the junction proteins in the fibrotic scar tissue served as epithelial markers, and then examined by Western blotting as in FIG. 21 and by immunostaining as in FIG. 22.

As is apparent from the data of FIGS. 21 and 22, AKAP12-knockout (KO) mice were found to express decreased levels of ZO-1, Occludin, and Ecadherin, which are essential for the physiological barrier, and also decreased levels of $\alpha$-SMA, compared with wild-type (WT) mice.

These results indicate that TGF-$\beta$1 and RA together increase the expression of AKAP12, so that the epithelial properties of the cerebral meninges which make it both a physiological barrier and a fibrotic scar even in the presence of TGF-$\beta$1 can be retained.

Hypoxia, a main EMT inducer, may be, for the most part, generated when oxygen is supplied due to damage having been done to the central nervous system and microvessels. In a later phase of hypoxia, active vascularization occurs to replenish the lesions with O2. As can be seen in FIG. 6, the expression of AKAP12 in the lesion decreases 3 days after cerebral injury, but increases 21 days post injury. To examine the vascularization of microvessels after cerebral injury, the expression pattern of the vascular endothelial marker CD31 in the brains of the mice was analyzed at 3 and 21 days after cerebral injury. The brain of a normal mouse was used as a control. The results are shown in FIG. 23.

Figure 23:
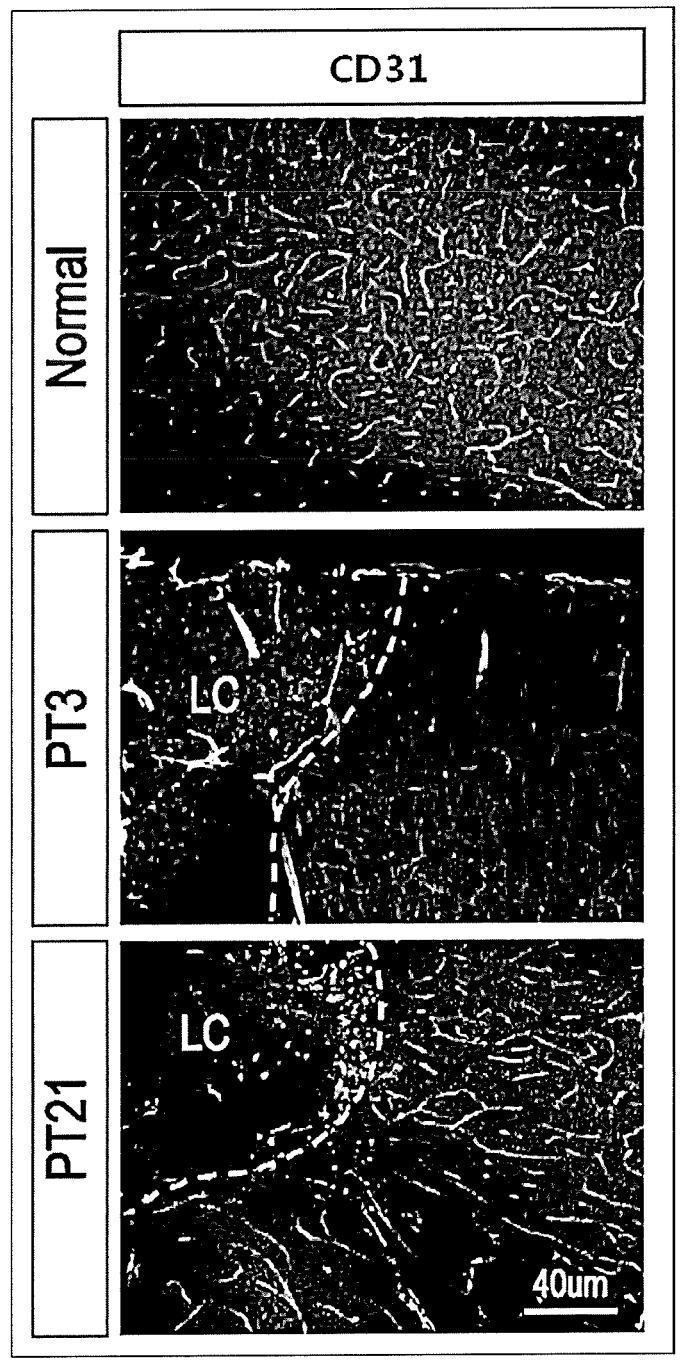
FIG. 23 shows vascularization around the lesion after 21 days.

As can be seen in FIG. 23, severe damage occurred to microvessels 3 days after cerebral injury and new vessels were generated around the lesion at 21 days post-injury. This result indicates the injury of microvessels causes hypoxia, leading to the inability to regulate the expression of AKAP12. In order to ascertain this, ARPE-19 cells were incubated for 24 hours in the absence of serum and then treated for an additional 48 hours with TGF-$\beta$1 (10 ng/mL) and RA (10 $\mu$M) under a 20% oxygen atmosphere, a 1% oxygen atmosphere or a 24 hr reoxygenation (20%) condition. The expression of AKAP12 and EMT marker was ascertained by Western blotting, and the results of AKAP12 were quantitatively analyzed. The results are given in FIG. 24.

Figure 24:
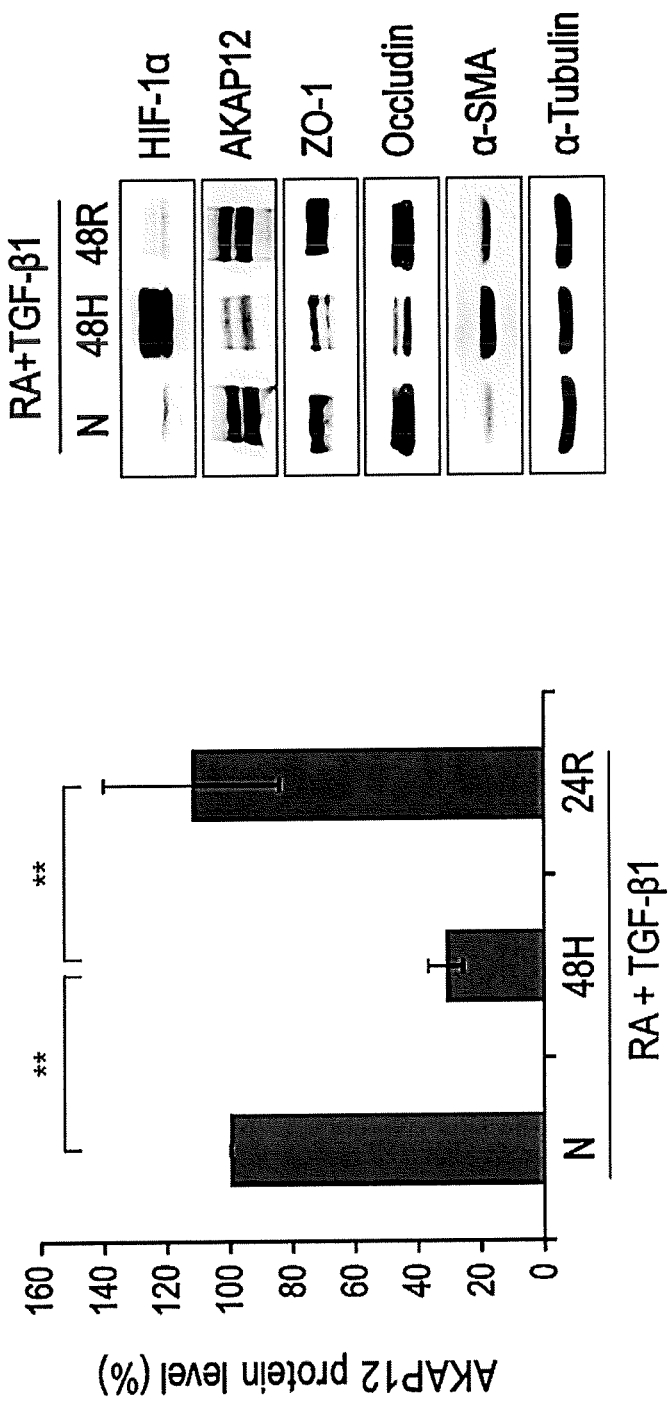
FIG. 24 shows the regulation of EMT depending on the concentration of O2.

In the presence of both RA and TGF-$\beta$1 under hypoxic conditions, as can be seen in FIG. 24, the expression of AKAP12 was decreased while the expression of EMT was decreased. Oxygen resupply was found to countervail this phenomenon. Thus, these results indicate that the expression of AKAP12 is controlled according to the O2 concentration.

Taken together, the data obtained above demonstrate that AKAP12 is a main factor in regulating EMT in the cerebral meninges after injury of the central nervous system. The immediate reconstitution of the cerebral meninges, which functions to protect the central nervous system against the external environment, is very important in minimizing additional injuries which would be otherwise generated. Hence, the high expression of TGF-$\beta$1 and RA is considered to be a "stand-by" mechanism. The high expression promotes EMT such that the cerebral meninges can be immediately reconstituted upon injury to the central nervous system. As the cerebral injury occurs, we believe that the O2 concentration changes to regulate the expression of AKAP12, thus finally regulating EMT.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The expression or activity regulator of AKAP12 in accordance with the present invention is expected to be used in the treatment and prognosis improvement of central nervous system diseases including post-traumatic stress syndrome, stroke, and spinal injury.

The invention claimed is:

1. A method of reducing inflammation-induced secondary injury in the central nervous system of a subject in need thereof by forming fibrotic-glial scars, the method comprising administering to the subject a composition comprising a pharmaceutically effective amount of TGF-β1 (transforming growth factor-beta 1) and retinoic acid as an activator of AKAP 12 (A-kinase anchoring protein 12) under oxygenated conditions to form fibrotic-glial scars, wherein the subject's level of inflammation-induced secondary injury is reduced following administration of TGF-β1 and retinoic acid compared to the subject's level of inflammation-induced secondary injury in the absence of TGF-β1 and retinoic acid.

2. The method of claim 1, further comprising administering an anti-inflammatory agent to the subject.

3. The method of claim 1, wherein the route of administration of the composition to the subject is oral, intra-arterial, intravenous, transdermal, intranasal, transbronchial, or intramuscular.

* * * * *